US012788436B2

(12) United States Patent
Ray et al.

(10) Patent No.: US 12,788,436 B2
(45) Date of Patent: Nov. 10, 2026

(54) DEVICES AND METHODS FOR LAPAROSCOPIC ACCESS AND WOUND CLOSURE

(71) Applicants: Subir Ray, Oakley, KS (US); Kuowei Chang, Lexington, MA (US)

(72) Inventors: Subir Ray, Oakley, KS (US); Kuowei Chang, Lexington, MA (US)

( * ) Notice: Subject to any disclaimer, the term of this patent is extended or adjusted under 35 U.S.C. 154(b) by 770 days.

(21) Appl. No.: 17/999,652

(22) PCT Filed: May 26, 2021

(86) PCT No.: PCT/US2021/034277
§ 371 (c)(1),
(2) Date: Nov. 22, 2022

(87) PCT Pub. No.: WO2021/242875
PCT Pub. Date: Dec. 2, 2021

(65) Prior Publication Data

US 2023/0285050 A1 Sep. 14, 2023

Related U.S. Application Data

(60) Provisional application No. 63/101,958, filed on May 26, 2020.

(51) Int. Cl.

| | |
|---|---|
| ***A61B 17/34*** | (2006.01) |
| ***A61B 17/00*** | (2006.01) |
| ***A61B 17/04*** | (2006.01) |
| ***A61M 13/00*** | (2006.01) |

(52) U.S. Cl.
CPC ...... *A61B 17/3474* (2013.01); *A61B 17/0469* (2013.01); *A61B 17/3496* (2013.01); *A61B 17/3498* (2013.01); *A61M 13/003* (2013.01); *A61B 2017/00349* (2013.01); *A61B 2017/00637* (2013.01); *A61B 2017/00663* (2013.01); *A61B 2017/3454* (2013.01)

(58) Field of Classification Search
CPC .............. A61M 17/3474; A61M 13/00; A61M 13/003; A61B 2017/00349; A61B 17/0469; A61B 17/3496; A61B 17/3498; A61B 2017/00637; A61B 2017/00663
USPC .......................................................... 604/26
See application file for complete search history.

(56) References Cited

U.S. PATENT DOCUMENTS

| | | | |
|---|---|---|---|
| 4,617,933 | A | 10/1986 | Hasson |
| 4,808,168 | A | 2/1989 | Warring |
| 5,137,509 | A | 8/1992 | Freitas |
| 5,330,488 | A | 7/1994 | Goldrath |
| 5,364,365 | A | 11/1994 | Wortrich |

(Continued)

OTHER PUBLICATIONS

International Search Report for PCT Patent Application No. PCT/US2021/034277, issued Sep. 16, 2021.

*Primary Examiner* — Philip E Stimpert
(74) *Attorney, Agent, or Firm* — King & Spalding

(57) ABSTRACT

The present invention provides devices and methods for laparoscopic access and wound closure. The device is in the form of a unitary needle device, which enables performance of several tasks, including penetration or puncture of fascia layers, insufflation of a body cavity with gas, and placing a suture for wound closure. In particular, the device features a blunt-tipped stylet having a hook or notch at the proximal end, which can be used to capture a suture.

20 Claims, 21 Drawing Sheets

(56) References Cited

U.S. PATENT DOCUMENTS

| | | | | | |
|---|---|---|---|---|---|
| 5,364,410 | A * | 11/1994 | Failla | A61B 17/3496 606/135 |
| 8,523,817 | B2 | 9/2013 | Mohajer | |
| 9,033,872 | B2 | 5/2015 | Mohajer-Shojaee | |
| 9,492,163 | B2 | 11/2016 | Bagaoisan | |
| 9,636,104 | B2 | 5/2017 | Mohajer-Shojaee | |
| 9,918,712 | B2 | 3/2018 | Malkowski et al. | |
| 10,512,454 | B2 | 12/2019 | Heneveld | |
| 10,660,636 | B2 | 5/2020 | Heneveld | |
| 2006/0074374 | A1 * | 4/2006 | Gresham | A61B 17/3474 604/26 |
| 2013/0324803 | A1 * | 12/2013 | Mohajer | A61M 13/003 600/249 |
| 2015/0038994 | A1 * | 2/2015 | Prior | A61B 17/3417 606/147 |
| 2015/0157317 | A1 * | 6/2015 | Bagaoisan | A61B 17/0485 606/148 |

* cited by examiner

DEVICES AND METHODS FOR LAPAROSCOPIC ACCESS AND WOUND CLOSURE

CROSS REFERENCE TO RELATED APPLICATIONS

This application is a national phase application under 35 U.S.C. § 371 of International Application No. PCT/US2021/034277, filed May 26, 2021, which claims priority to U.S. Provisional Application No. 63/101,958, filed May 26, 2020. The contents of each of the above-identified applications are hereby fully incorporated herein by reference.

FIELD OF THE ART

The present invention relates to devices, methods, systems, and kits for safe laparoscopic access and wound closure in a patient in need thereof. The devices, methods and systems can be used to safely penetrate a patient's body wall for laparoscopic surgery, insufflate a body cavity with gas, and place sutures for wound closure. This invention enables performance of these important tasks that normally would require usage of a multitude of special devices. In particular, the device is a unitary needle device that comprises a hook for suture capture.

BACKGROUND

In laparoscopic surgery, access of patient's peritoneal cavity and creation of pneumoperitoneum is commonly performed by using a Veress needle. The cannula of a Veress needle is a sharp, beveled, stainless steel needle tip for cutting through tissues of the abdominal wall. Inside the cannula, there is a spring-loaded, hollow stylet with a rounded blunt tip to protect any viscera from injury by the sharp, piercing cannula. In rest position, the rounded blunt tip protrudes slightly beyond the sharp tip of the cannula. The stylet is made of a hollow tube used for transferring gas (e.g., carbon dioxide gas) to create pneumoperitoneum for laparoscopic surgery. The tips of the cannula, hollow stylet, and the assembled cannula/stylet are shown in FIG. 1.

As the Veress needle penetrates the peritoneal wall, the direct contact pressure exerted by tissue on the tip area pushes the stylet into the inner lumen of the cannula, exposing the sharp cannula to penetrate the tissue wall. After the needle tip pierces through the skin/fascia and enters the peritoneal cavity, the rounded-end, blunt stylet rapidly springs forward to block the sharp cutting tip and protect internal viscera from injury by the sharp cannula. The penetration of Veress needle into the peritoneal cavity carries unique audio-vibrational feedback to the surgeon (FIG. 2).

After the Veress needle enters the cavity, gas (e.g., carbon dioxide gas) can then be transferred through the hollow lumen of the stylet to inflate the peritoneal space, creating a pneumoperitoneum for ease of laparoscopic surgery.

Trocars and probes may also be inserted into the peritoneal cavity during laparoscopic surgery. At conclusion of laparoscopic surgery, the Veress needle, trocars, and probes are retracted, leaving open wounds to be closed by suture. The process of suturing the various peritoneal layers including skin and fascia layers are laborious and is therefore omitted for small wounds. The potential risks of such include infection and subsequent development of incisional hernia. The method of peritoneal fascial closure normally requires use of a separate device to mechanically approximate the edge of an internal wound or incision with suture. A suture is introduced and externalized by a separate device from inside the peritoneal space across the wound location. The two ends of a suture are then pulled up, tightened, and knotted from outside to complete the closure of a wound left by the device such as a trocar. There are many wound closure devices marketed for laparoscopic surgery. Most of those devices are costly and complicated mechanical instruments. Certain devices can enter the peritoneal cavity following the same technique as a Veress needle, but the stylet is made of a solid rod and it cannot pass $CO_2$ gas for creation of the pneumoperitoneum. Further, the device is designed to only capture a suture and deliver it internally or externally through the abdominal wall. As an example, the Covidien Endo Close™ or Auto Suture™ device is equipped with a spring-loaded push button to advance the stylet forward to facilitate suture capturing inside the peritoneal cavity.

There remains a need for devices, methods, and systems for safe and efficient laparoscopic access and wound closure in patients in need thereof. In particular, there is a need for a single, or unitary, device that is capable of laparoscopic access, insufflation of a body cavity, and would closure in patients in need thereof.

The description herein of certain advantages and disadvantages of known devices, methods, and systems is not intended to limit the scope of the embodiments.

SUMMARY

It is an object of the present invention to provide a device—in some embodiments a needle and stylet assembly—for penetrating a body cavity through a body wall to form an opening and thereafter drawing sutures through the opening to close off a proximal wound (i.e., a wound near the device entry location that was formed by another device such as a laparoscopic surgical device (e.g., a trocar)). It is a further object of the present invention to provide a device for insufflating the body cavity with gas.

It is another object of the present invention to provide methods for penetrating a body cavity through a body wall to form an opening and thereafter drawing sutures through the opening to close off a proximal wound. In certain embodiments, the methods may further include insufflating the body cavity with gas.

It is another object of the present invention to provide kits that include a device—in some embodiments the kit may include, among other things, a needle and stylet assembly—for use in a procedure involving penetrating a body cavity through a body wall to form an opening and thereafter drawing sutures through the opening to close off a proximal wound. It is a further object of the present invention to provide a kit that includes a device for insufflating the body cavity with gas.

One aspect of the present invention is to provide a device or assembly comprising a cannula having a cannula distal end and a cannula proximal end. In preferred embodiments the cannula is hollow and therefor has an internal lumen. In certain embodiments, the cannula includes a housing unit at the cannula distal end. In some embodiments, the housing unit also includes an internal hollow lumen. Further, in certain embodiments, the cannula includes a beveled needle tip at the cannula proximal end.

Another aspect of the present invention is to provide a device or assembly comprising a stylet—e.g., a blunt-tipped stylet—having a stylet proximal end and a stylet distal end, wherein the stylet is configured to be inserted into an internal lumen of (i.e., inserted within), and supported by, the cannula. In certain embodiments the stylet includes a hook at the stylet proximal end. In other embodiments, the stylet includes a notch at the stylet proximal end.

Another aspect of the present invention is to provide a device or assembly comprising a gas valve for introduction of gas at the proximal end of the cannula. In certain embodiments, the gas valve is positioned distal to the housing unit.

A further aspect of the present invention is to provide a device or assembly comprising a front compression spring. In certain embodiments, the front compression spring encompasses the stylet distal end. For example, the front compression spring is coiled or wrapped around the outer wall of a portion of the stylet near the distal end of the stylet.

Another aspect of the present invention is to provide a device or assembly comprising a spring cassette. In certain embodiments, the spring cassette comprises a rear compression spring; a blocking ring with at least two pins protruding outward, which is distal to the rear compression spring; a distal cassette endcap that is distal to the blocking ring; a tubular support flanked by a proximal cassette endcap and by the gas valve on the distal end, situated in the interior of the rear compression spring, the blocking ring and the distal cassette endcap.

In certain embodiments of the present invention, the device or assembly may be assembled by inserting the stylet, front compression spring and spring cassette through the distal end of the housing unit (i.e., through the housing unit's internal lumen) and into the cannula (i.e., through the cannula's internal lumen) so that the stylet proximal end protrudes beyond the needle tip located at cannula proximal end.

In some embodiments of the present invention, the housing unit further comprises at least one, but preferably at least two (i.e., a plurality of) side slots. In certain embodiments, the side slots are configured to accept the at least two pins protruding outward from the blocking ring of the spring cassette.

In certain aspects of the present invention, the stylet may retract into the internal lumen of the cannula. In certain embodiments, the stylet retracts into the cannula when the device or assembly is pressed into a body wall of a patient.

In other aspects of the present invention, the stylet is configured to spring forward beyond the cannula tip after the cannula tip has penetrated through the body wall and into a body cavity. In certain embodiments, the action of the stylet springing forward is governed by the spring cassette. For example, in certain embodiments, the stylet may spring forward automatically once the cannula tip has penetrated through the body wall.

Aspects of the present invention also include a component to facilitate the flow of insufflation gas, such as a gas valve or stopcock. In certain embodiments, the gas valve is located distal to the housing unit. In some embodiments, the gas valve or stopcock is mounted on the housing unit. Embodiments of the present invention also involve introducing insufflation gas into the body cavity through the gas valve or stopcock and through the stylet.

In certain aspects of the present invention the stylet includes a feature for capturing and maneuvering a suture, such as a hook or notch. In some embodiments, the feature (i.e., the hook or notch) can be retracted backward to lock in or capture a suture. Generally, during suture capture, the hook or notch does not retract completely into the lumen of the cannula.

Methods of use of the devices and assemblies in laparoscopic access and wound closure in a patient in need thereof are also disclosed herein.

BRIEF DESCRIPTION OF THE DRAWINGS

The subject matter regarded as the invention is particularly pointed out and distinctly claimed in the concluding portion of this specification. The invention, however, both as to organization and method of operation, together with objects, features, and advantages thereof, may best be understood by reference to the following detailed descriptions when read with the accompanying drawings in which:

FIG. 13B shows a closer view of the stopcock and push button.

Figure 1:
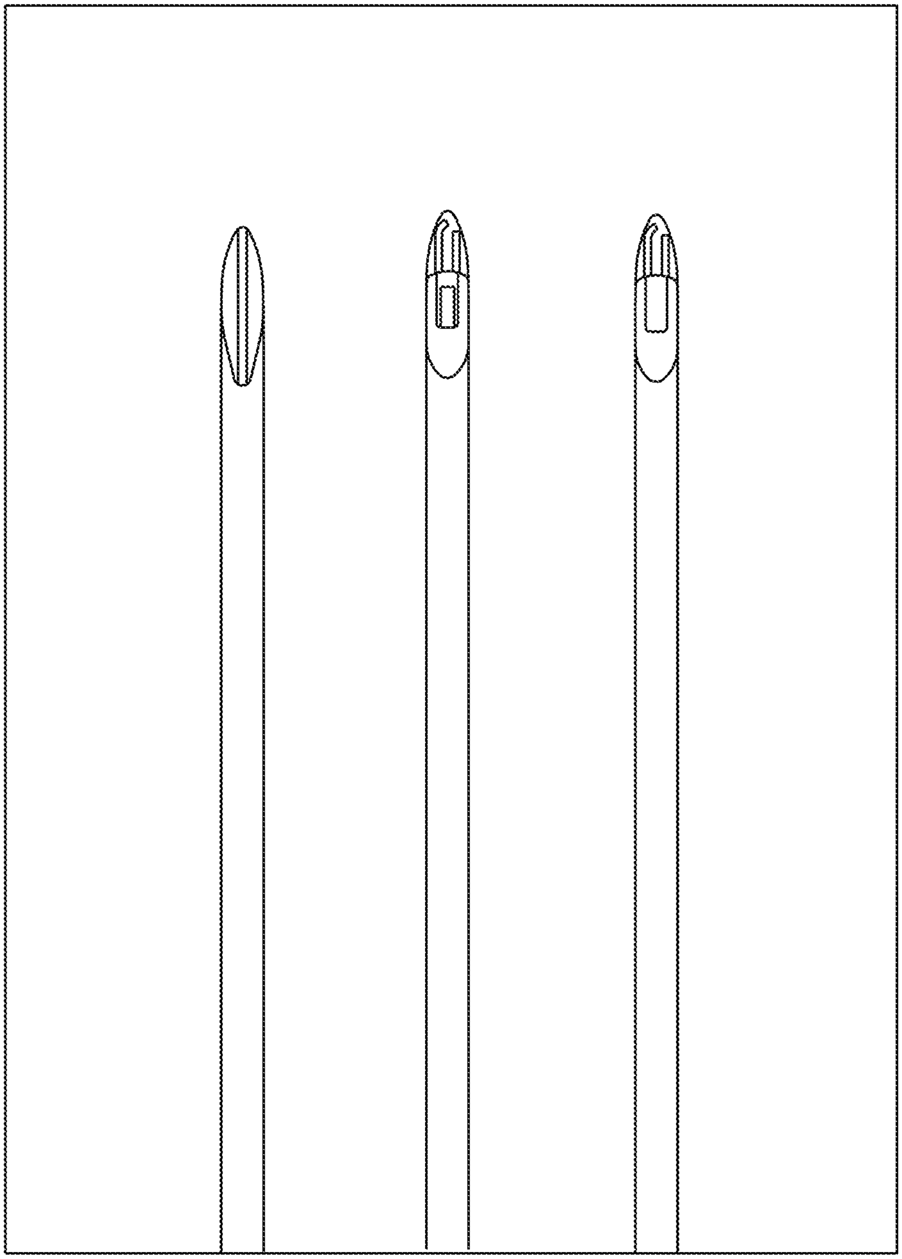
FIG. 1 is a photograph of the tips of the cannula, the stylet, and the assembled cannula/stylet.

It will be appreciated that, for simplicity and clarity of illustration, elements shown in the figures have not necessarily been drawn to scale. For example, the dimensions of some of the elements may be exaggerated relative to other elements for clarity. Additionally, the many features of any one embodiment shown in a figure should not be considered independent and separate from the features of an embodiment shown in another figure, and it is conceivable that features of any one embodiment may be combinable with another. Further, where considered appropriate, reference numerals may be repeated among the figures to indicate corresponding or analogous elements. Moreover, the arrows and braces used to point to different parts and portions of the embodiments shown in the figures are approximate only and should not be considered limiting in any way.

DETAILED DESCRIPTION

In the following detailed description, numerous specific details are set forth in order to provide a thorough understanding of the invention. It will be understood by those of ordinary skill in the art, however, that the present invention may be practiced without these specific details. In other instances, well-known methods, procedures, and/or components have not been described in detail so as not to obscure the present invention. Further, it will be understood by those of ordinary skill in the art that the invention(s) disclosed herein should not be limited to any one specific embodiment and that different embodiments may be contemplated, including embodiments that contain all or part of the specifically described embodiments or that contain a mixture of components of the several specific embodiments described herein.

Further, the present invention is described in the context of exemplary embodiments. The scope of the invention, however, is not limited to the particular examples and embodiments described in the specification. Rather the specification merely reflects certain embodiments and serves to illustrate the principles and characteristics of the present invention. Those skilled in the art will recognize that various modifications and refinements may be made without departing from the spirit and scope of the invention.

The present invention provides devices and methods for safe laparoscopic access and wound closure in a patient in need thereof. Devices according to certain embodiments can be used to accomplish safe penetration of a patient's body cavity, such as a peritoneal wall, for laparoscopic surgery. The devices of the present invention also allow for the creation of pneumoperitoneum via gas insufflation and efficient wound closure using suture.

The skyrocketing cost of healthcare is an area of great concern and containing hospital costs is of great importance. Surgical instruments that provide multiple functions is an effective way to curtail such costs. Concomitant reduction in surgical device procurement, inventory costs, and sterilization expenses are some of the direct benefits. Shorter surgery time, better efficiency in the operating room, greater safety for the patient, and improved device reliability may reduce the overall expenses of surgical procedures. The present invention helps to reduce costs by, among other things, combining the functionality of a Veress needle and the trocar site closure device into a single unitary surgical instrument.

As referred to herein, "proximal" means nearer to the point of attachment or insertion into the body and "distal" means refers situated away from the point of attachment or insertion into the body.

Devices

According to certain embodiments, the present invention includes a device 10 for penetrating a body cavity through a body wall to form an opening in a patient, insufflating the cavity with gas through the opening, and drawing sutures through the opening to close off a proximal wound, for example, a wound created by penetration with a surgical device such as a trocar device. After retraction of the trocar device, the resulting wound can be closed with sutures through a process facilitated by a device 10 according to certain aspects of the invention.

In certain embodiments, the device 10 comprises a cannula 11. In preferred embodiments, the cannula 11 is an elongated sleeve having a hollow lumen extending along its length.

In some embodiments, the cannula includes a housing unit 12 located at a distal end of the cannula 11 and a beveled needle tip 110 located at a proximal end of the cannula. In some embodiments, the housing unit 12 is formed integral with the cannula 11, while, in other embodiments, the housing unit 12 and cannula 11 may be separate components that are connected (i.e., affixed or attached) together via means well known in the art such as, e.g., a screw, threaded connection, or adhesives.

In certain embodiments, the device 10 of the present invention comprises a blunt-tipped stylet 13. The blunt tip 130 of the stylet 13 can be flat or rounded but is not sufficiently sharp to damage body tissue with gentle force. In certain embodiments, the stylet 13 is an elongated sleeve having a hollow lumen extending along its length. In other preferred embodiments, the stylet 13 includes a suture-capture feature, such as, e.g., a hook or notch 131, located at the proximal end of the stylet 13. According to certain aspects of the invention, the blunt-tipped stylet 13 may be inserted into the hollow lumen of the cannula 11 and may be supported within the cannula 11.

In certain embodiments, the device 10 of the present invention further comprises a gas valve 16. In some embodiments, the gas valve 16 is positioned distal to the housing unit 12. In preferred embodiments, the gas valve 16 is configured to introduce gas at the proximal end of the cannula 11. The gas may be used to insufflate a body cavity of a patient.

In certain embodiments, the device 10 of the present invention also comprises a front compression spring 14. In preferred embodiments, the front compression spring 14 encompasses (i.e., is coiled about or wrapped around) the distal end of the stylet 13.

In certain embodiments, the device 10 of the present invention further comprises a spring cassette 15. The spring cassette 15 includes various components that operate to maneuver the blunt-tipped stylet 13 between a retracted configuration and an extended configuration within the cannula 11. For example, according to certain aspects of the present invention, the spring cassette 15 may include a rear compression spring 150, a blocking ring 151, a distal cassette endcap 153, a tubular support 154, and a proximal cassette endcap 155. In certain embodiments, the blocking ring 151 may be located distal to the rear compression spring 150. Further, in some embodiments, the blocking ring 151 may include at least two pins 152 protruding outward (i.e., laterally away from) the blocking ring 151. In certain embodiments, the distal cassette endcap 153 of the spring cassette 15 is located distal to the blocking ring 151. Additionally, in certain embodiments, the tubular support 154 flanks (i.e., is adjacent to or abuts) the proximal cassette endcap 155 as well as the gas valve 16 that is located, in some embodiments, distal to the housing unit 12. In one embodiment, the tubular support 154 is situated (i.e., located or positioned) in the interior of the rear compression spring 150, the blocking ring 151, and the distal endcap 153.

Moreover, according to certain aspects of the present invention, the stylet 13, front compression spring 14, and spring cassette 15 may be inserted through the distal end of the housing unit 12 and into the cannula 11 (i.e., into the hollow lumen of cannula 11). Typically, the stylet 13, together with the front compression spring 14 and spring cassette 15, are inserted into the hollow lumen cannula 11 such that the proximal end of the stylet 13 protrudes beyond the beveled needle tip 110 of the cannula 11. In this way, when the proximal end (including stylet tip 130) of the stylet 13 protrudes beyond the beveled needle tip 110 of the cannula 11, the stylet 13 can be said to be in the extended configuration. Further, when in the extended configuration, the stylet 13 operates to block the needle tip 110 of the cannula 11 to prevent the needle tip 110 from injuring viscera or other aspects of the body cavity.

In certain embodiments, the housing unit 12 comprises at least two side slots 120 into which fit the at least two pins 152 protruding outward from the blocking ring 151.

Further, according to certain aspects of the present invention, the stylet 13 has a retracted configuration in which the stylet 13 retracts into the hollow lumen of the cannula 11. When in the retracted configuration, the beveled needle tip 110 of the cannula 11 is exposed to allow puncturing the skin of a patient.

According to certain aspects, the extended configuration—where the stylet 13 extends beyond the needle tip 110 of the cannula 11—is the primary configuration of the device 10 of the present invention. In other words, the device 10 naturally maintains the extended configuration without any involvement of a user, although other embodiments in which the device 10 naturally maintains the retracted configuration are also contemplated. In certain embodiments, in order to alter the device 10 of the present invention from the extended configuration to the retracted configuration, the user must press the blunt-tipped stylet 13 against a surface, such as, e.g., the surface of a patient's skin, to force the stylet 13 into the cannula 11. In other embodiments, in order to alter the device 10 from the retracted configuration to the extended configuration, the force applied against the tip of the stylet 13 must be substantially reduced, such as when the stylet 13 tip enters the abdomen, or the user must cease applying forward force, such as upon receiving the audio and vibrational feedback when the stylet 13 tip enters the abdomen. For example, in preferred embodiments, the stylet 13 is spring-loaded within the cannula 11 such that the rear spring forces the tip 130 of the stylet 13 out of the cannula 11—i.e., into the extended configuration—whenever a force is not applied to push the tip 130 into the cannula 11. In this way, when the beveled needle tip 110 of the cannula 11 penetrates through the body wall and into the body cavity, wherein the stylet 13 springs forward beyond the beveled needle tip 110 of the cannula 11. Although the stylet 13 will move forward automatically to prevent visceral injury, as soon as the tissue resistance on the stylet 13 tip subsides, the user should stop pushing the device 10 forward, as audio and vibrational feedback indicates that the device 10 has penetrated the body wall and entered the body cavity.

In certain embodiments of the present invention, the gas valve and stylet 13 are each configured to introduce insufflation gas into a body cavity. That is, insufflation gas can be introduced through the gas valve and through the internal hollow lumen of the stylet 13 to be released within the body cavity.

According to certain aspects of the present invention, the stylet 13 comprises a suture-capturing feature such as, e.g., a hook or a notch 131. In certain embodiments, the hook or notch 131 of the stylet 13 may be retracted, e.g., automatically, into the resting position to capture or hold a suture when the user ceases to push the stylet 13 forward. For example, in certain embodiments, the hook or notch 131 moves a short distance back to the closed or resting position (FIG. 9B and FIG. 10) to form a gap to capture the suture. In certain embodiments, the hook or notch moves a distance of about 0.1" to about 0.15", or about 0.12", to form a gap to capture the suture. Generally, the hook or notch 131 moves substantially inside the cannula 11 lumen only when puncturing the abdominal wall.

In certain embodiments, the device 10 further comprises an extension tube 17 and a gas connector 18, which serves as an angled (e.g., right-angle) adaptor between the extension tube 17 and the gas valve 16 (see FIGS. 12, 13, 14, and 16). In some embodiments, the extension tube 17 connects the distal end of the stylet 13 to the gas connector 18. According to certain aspects of the present invention, the gas connector 18 is a hollow piece with an opening for the extension tube 17 and an opening for the gas connector 18 positioned such that the gas valve 16 (or stopcock) is mounted on the connector 18 at approximately a right angle (90°) to the extension tube 17 and stylet 13. In certain embodiments, the extension tube 17 and gas connector 18 are considered part of the stylet assembly 20, though other configurations are possible. In some embodiments, when the stylet assembly 20, including the extension tube 17 and gas connector 18, is inserted into the cannula 11 and housing unit 12, the gas connector 18 is positioned distal to the housing unit 12.

In certain embodiments, the gas valve 16 is a stopcock. In one embodiment, the gas valve 16 is distally mounted on the housing unit 12 and in an axial position relative to the stylet 13. In another embodiment, the gas valve 16 is mounted on the gas connector 18 and in an orthogonal position relative to the stylet 13. In certain embodiments, a push button 19 is attached to the gas connector 18 (see FIG. 13). The push button 19 may be formed of any suitable material, such as, for example, plastic. The push button 19 can be used to assist with maneuvering of the stylet 13, during, for example, suture capture. In certain embodiments, when the gas valve 16 is mounted in an orthogonal position relative to the stylet 13, the stylet 13 can be easily pushed forward against the side of the gas connector 18 without a push button 19 because the gas valve 16 and gas tubing is no longer in the way (see FIG. 12).

In certain embodiments, the suture is captured using a hook or notch 131. The invention expressly contemplates embodiments where a hook 131 is used to capture the suture, as well as embodiments where a notch 131 is used. The hook or notch 131 allows passage of the suture into the hook or notch 131 and a curved wall to capture the suture.

In one embodiment, the at least two pins 152 protruding outward from the blocking ring 151 are screws, e.g., set screws. In another embodiment, the at least two pins 152 protruding outward from the blocking ring 151 are solid pins, e.g. non-threaded pins.

The insufflation gas may be any suitable gas for carrying out insufflation of a body cavity or for creating a pneumoperitoneum. In certain embodiments, the insufflation gas is carbon dioxide ($CO_2$).

In certain embodiments, the body cavity is a peritoneal cavity.

In certain embodiments, the device 10 is in the form of a unitary needle device. Generally, the device according to the embodiments enables performance of several tasks that would require usage of a multitude of special devices. Such tasks include, for example, penetration or puncture of fascia layers, insufflation of a body cavity with gas, and placing a suture for wound closure.

Figure 3A:
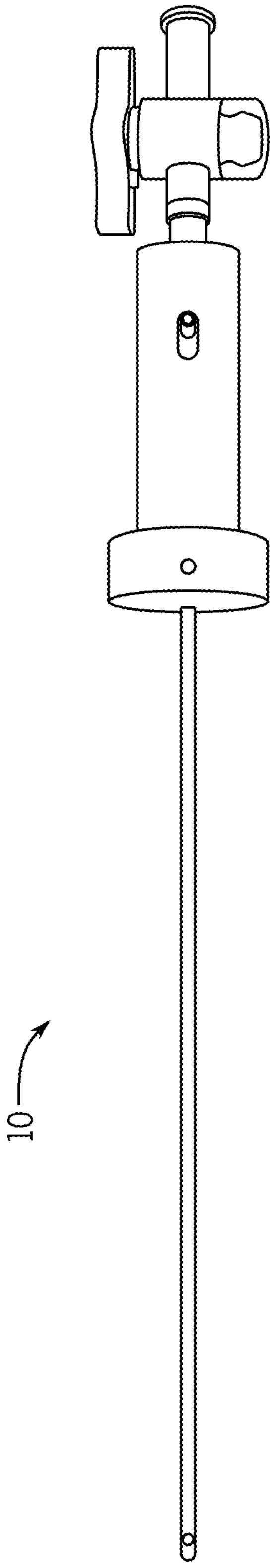
FIGS. 3A and 3B (collectively, FIG. 3) are top and side photographs of an exemplary device according to certain embodiments of the present invention.
Figure 3B:
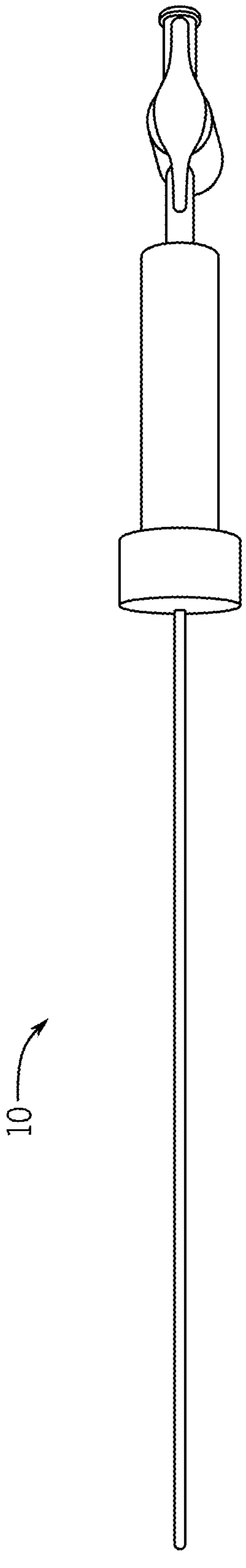
Figure 12A:
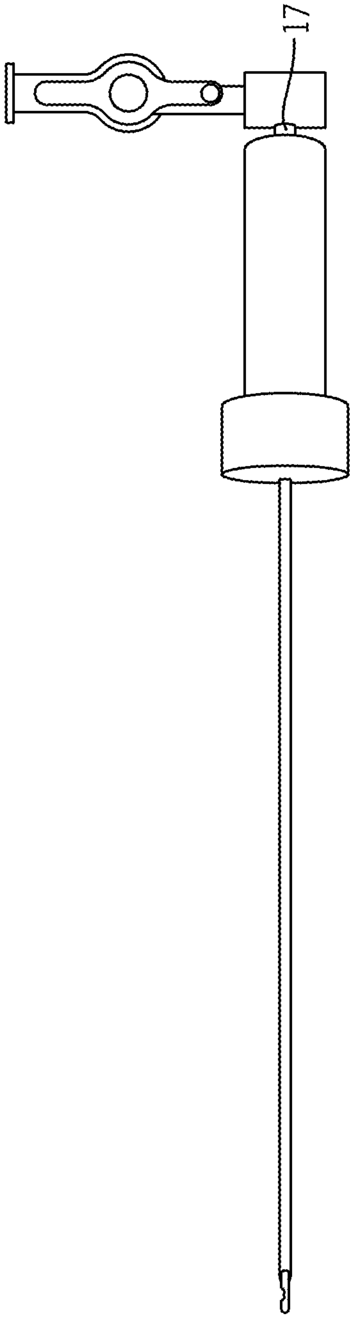
FIGS. 12A and 12B (collectively, FIG. 12) are photographs showing an exemplary device with the stopcock located at right angle to the stylet according to certain embodiments of the present invention.
Figure 12B:
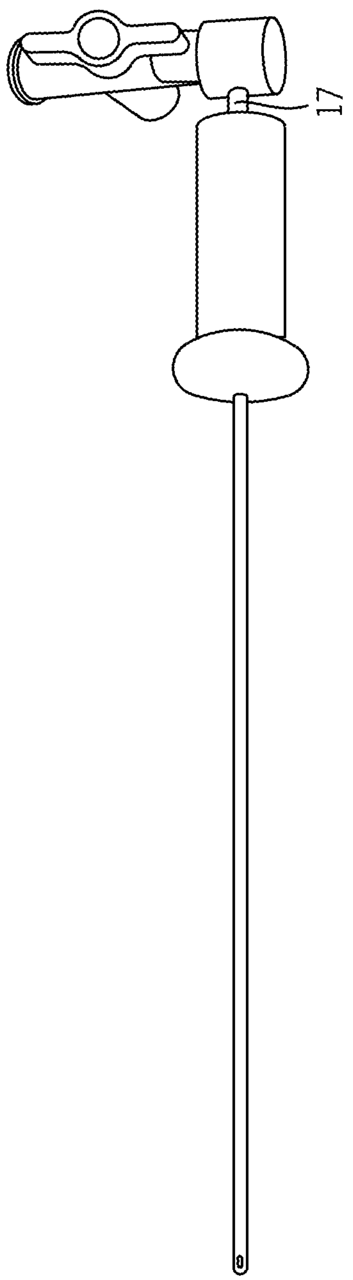
Figure 13A:
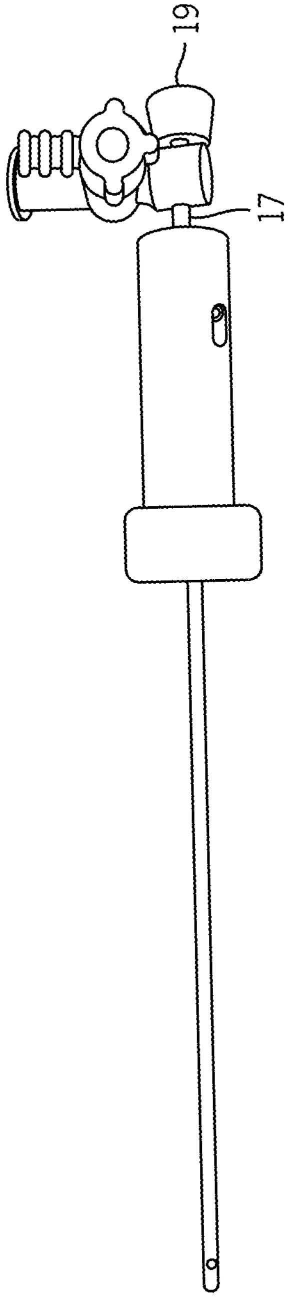
FIGS. 13A and 13B (collectively, FIG. 13) are photographs showing an exemplary device with the stopcock located at right angle to the stylet and including push button according to certain embodiments of the present invention.
Figure 13B:
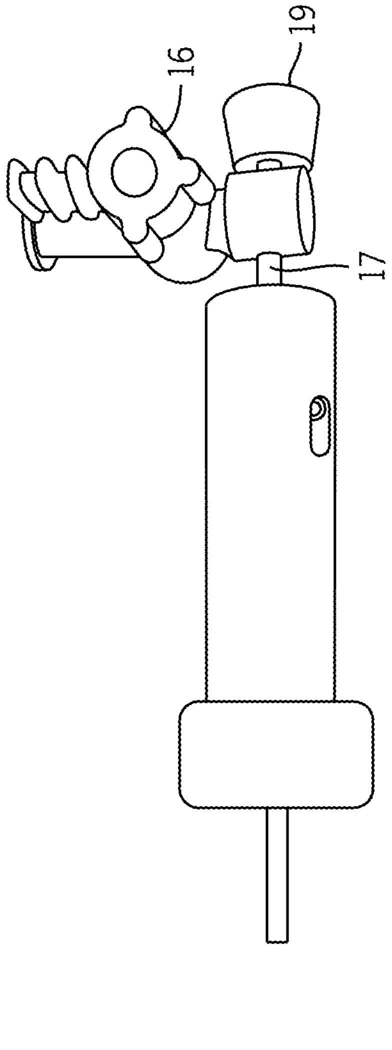
Figure 14:
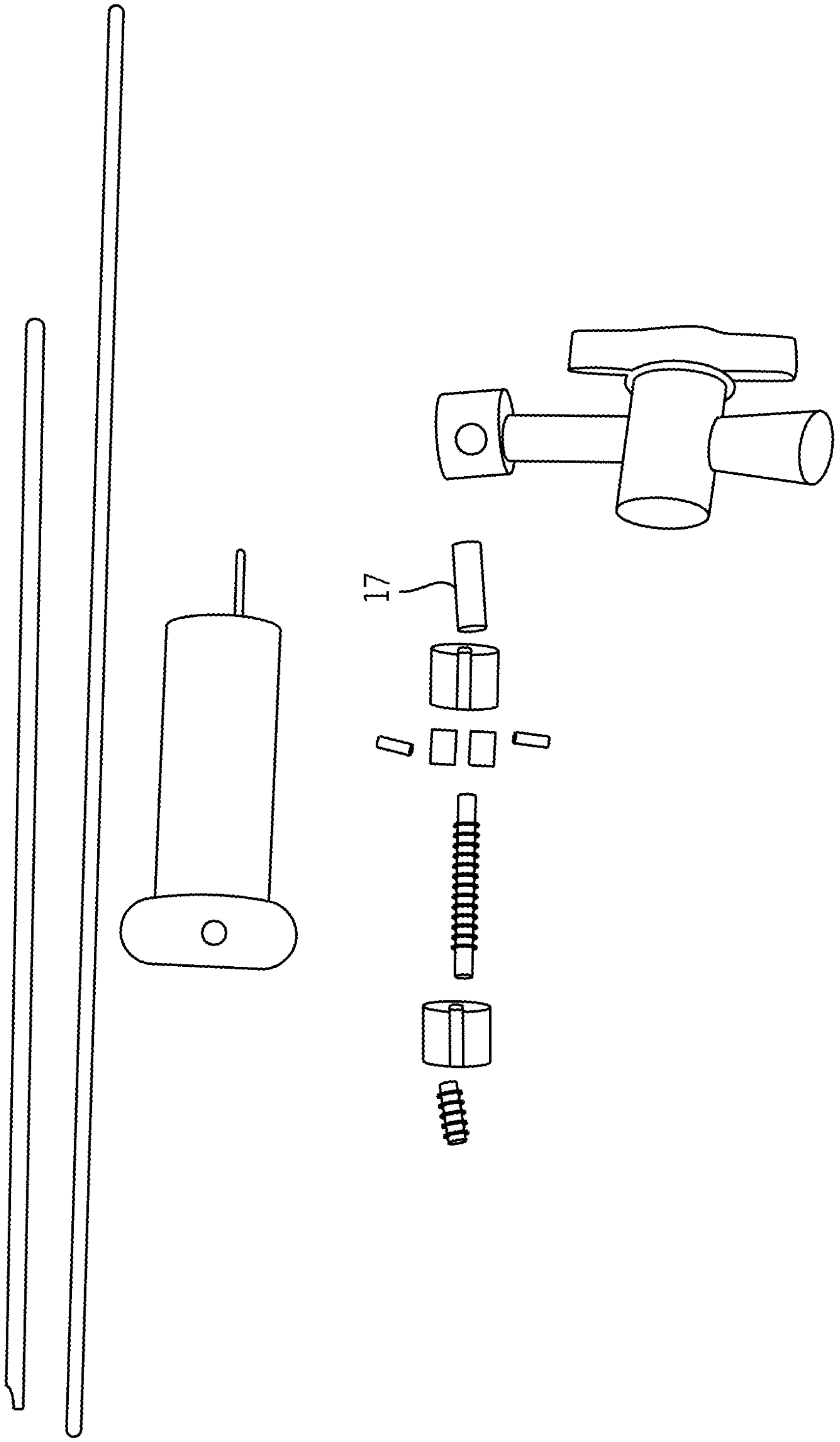
FIG. 14 is a photograph showing the components of an exemplary device prior to assembly according to certain embodiments of the present invention.
Figure 15:
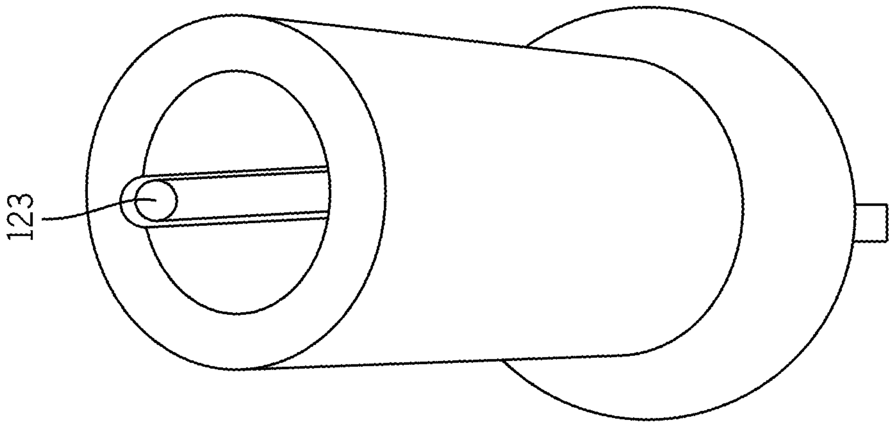
FIG. 15 shows a photograph of an exemplary anti-rotation dowel pin installed in an exemplary housing unit according to certain embodiments of the present invention.
Figure 16:
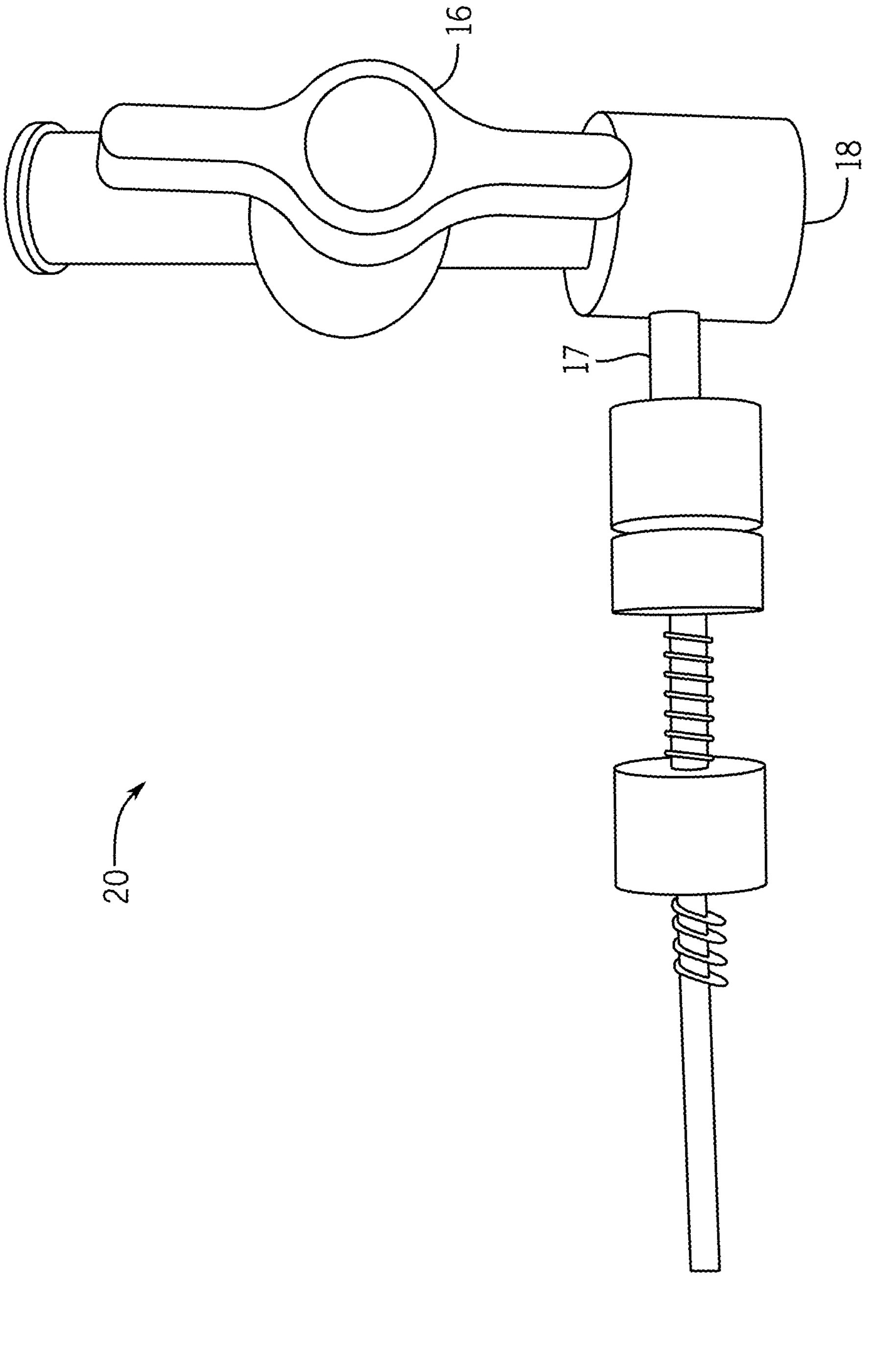
FIG. 16 shows a photograph of an exemplary stylet assembly according to certain embodiments of the present invention.

The exemplary devices described herein can be used to safely pierce the peritoneal wall, protect against viscera injury with a spring-loaded hollow stylet 13, and pass carbon dioxide gas through the stylet 13 lumen to create pneumoperitoneum for laparoscopic surgery, and introduce and place a suture for wound closure without requiring a separate device. An exemplary device is shown in FIGS. 3, 12, and 13.

The exemplary device can be inserted into a patient's peritoneal cavity by penetrating skin and fascia layers with the cannula 11 of the device 10. Direct pressure on the stylet tip 130, as when penetrating through the strong fascia layers, pushes the blunt- or round-ended stylet 13 into the shaft of the cannula 11. When the cannula tip 110 of the device 10 enters the peritoneal cavity, the tissue forces against the dull stylet tip 130 suddenly subsides and the stylet 13 rapidly springs forward thus shielding the tip of cannula 11 from damaging any viscera inside the cavity. Subsequently, gas (e.g., $CO_2$ gas) can be introduced through the device 10 and into the peritoneal cavity to insufflate the cavity. The peritoneal cavity is insufflated in preparation for and during laparoscopic surgery.

Figure 6A:
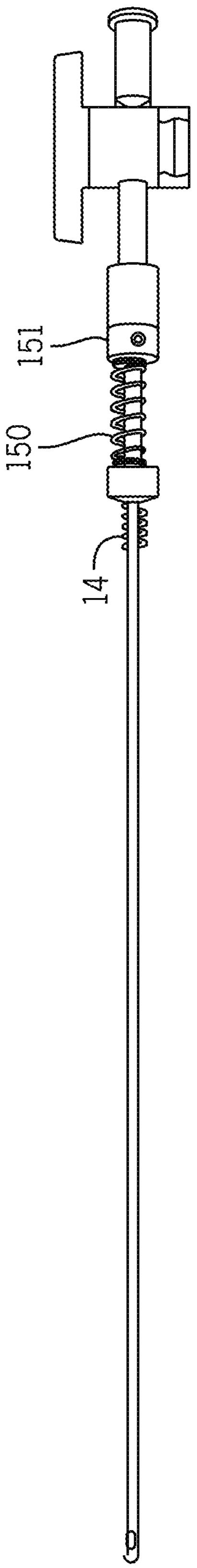
FIGS. 6A and 6B (collectively, FIG. 6) are top and side photographs of an exemplary stylet assembly according to certain embodiments of the present invention.
Figure 6B:

The device 10 utilizes two compression springs 14 and 150 (see FIG. 6). The rear compression spring 150 installed inside the cassette is used to push out the stylet 13. Direct contact pressure on the stylet tip 130, as when penetrating through fascia layers, pushes the stylet 13 into the shaft (or hollow lumen) of the cannula 11. That is, the device 10 of the present invention adopts the retracted configuration. When the cannula 11 enters the peritoneal cavity, the contact pressure subsides, and the stylet 13 springs forward, thereby shielding and blocking the sharp cutting tip 110 of the cannula 11. That is, the device 10 of the present invention adopts the extended configuration.

Figure 4A:
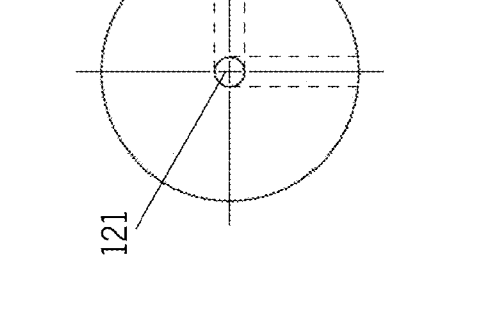
FIGS. 4A, 4B, and 4C (collectively, FIG. 4) are drawings showing an exemplary housing unit according to certain embodiments of the present invention.
Figure 4B:
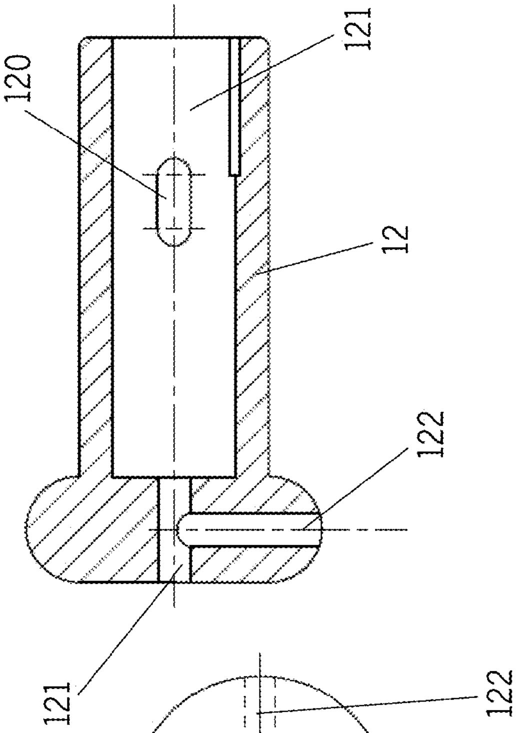
Figure 4C:
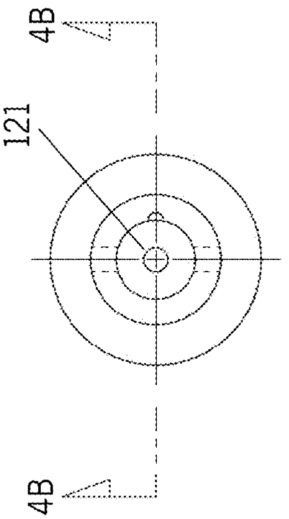
Figure 5C:
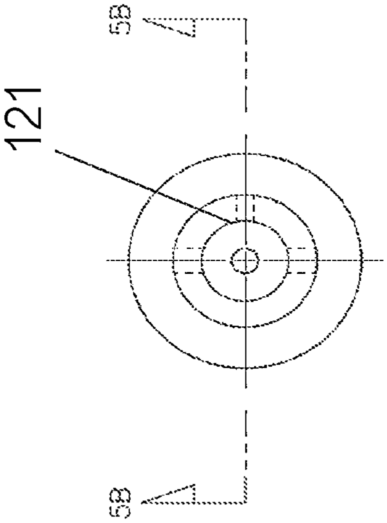
FIGS. 5A, 5B, and 5C (collectively, FIG. 5) are drawings showing an exemplary housing unit according to certain embodiments of the present invention.
Figure 5B:
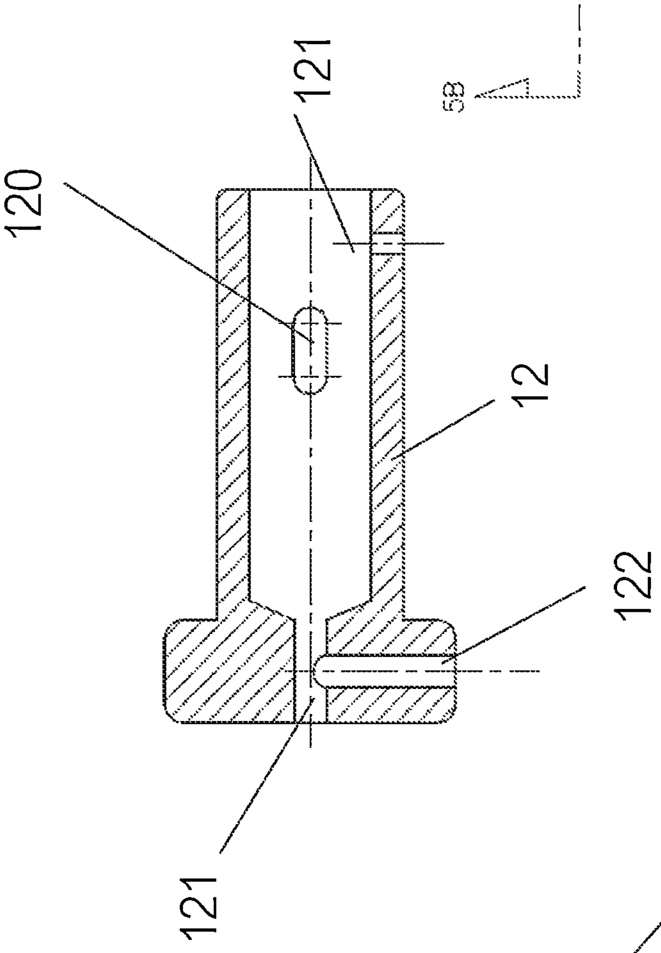
Figure 5A:
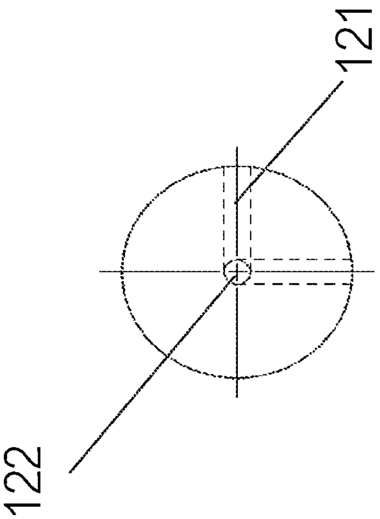

After laparoscopic surgery, the device 10 can be used for suture capturing, suture passing, and wound closure. The stylet 13 can be pushed forward via the gas valve 16 (or a button 19 or gas connector 18 affixed to the gas valve 16). The maximum travel distance of the stylet tip 130 is limited by the length of the side slots 120 of the housing unit 12 (FIGS. 4 and 5).

For ease of suture capture, the stylet assembly 20 is pushed forward into the extended configuration. After pushing forward, the hook or notch 131 of the stylet tip 130 is sufficiently distant from the end of the cannula 11 to create an opening for the suture to pass into (see FIG. 9). When the suture is caught or captured by the hook or notch 131, the front compression (or otherwise a second) spring 14 near the proximal side of the spring cassette 15 is used to retract the stylet 13 into the retracted configuration when the forward push is ceased. The front compression spring 14 pulls the hook or notch 131 into a position where the opening is covered by the outer cannula 11 and the suture is held in the space between the hook and the cannula 11. FIG. 10 shows the stylet tip 130 in the retracted position. After the suture is securely held, it is passed in and out of the abdominal wall around the wound to be closed by tying a knot from outside the abdomen. The wound is closed by tissue approximation, i.e., bringing tissue edges into desired position for suturing.

In certain embodiments, for suture capturing, the stylet 13 can be maneuvered, for example pushed forward and outward into the extended configuration, via the gas valve 16 (e.g., stopcock), gas connector 18, or a button 19 attached to the gas valve 16. Alternatively, in other embodiments, the position of the gas valve 16 can be shifted at right angle (i.e., orthogonal) to the stylet 13, thereby creating room for thumb activation or installation of a button 19 (FIGS. 12 and 13).

The description above is intended to illustrate the underlying principles and mode of operations of the device according to exemplary embodiments of the invention. Therefore, the device design and various drawings disclosed herein are not intended to represent or limit the commercial product to be manufactured, although the device as shown can indeed be produced and commercialized. In standard production engineering practice, molded plastic parts may be used to replace any machined parts as shown above in order to save labor and costs. The various parts exemplified in the Figures can be manufactured by injection molding processes.

A "cannula" as referred to herein is a hollow, elongated, cylindrical sheath terminating in a sharp cutting edge for piercing external body tissue of a patient.

The front portion of the exemplary device 10 consists of a cannula 11 with a beveled needle tip 110 used for piercing or puncturing a body wall, e.g. the abdominal wall. According to certain embodiments, the cannula 11 is a hollow tube with a beveled needle tip 110 at the proximal end. The beveled needle tip 110 is sharp. Generally, the cannula 11 includes a tubular passage configured to surround at least a portion of the length of the stylet 13. Most of the stylet 13 is housed inside the cannula 11. The proximal stylet tip 130 protrudes beyond the beveled needle tip 110 of the cannula 11 (i.e., in the extended configuration) when no force or pressure is applied to the stylet tip 130.

A cannula 11 according to certain embodiments may be made of any suitable material, such as, for example, metal or plastic. In certain embodiments, the cannula 11 is stainless steel, for example 304 stainless steel.

The cannula 11 can be any suitable gauge for laparoscopic use. In certain embodiments, for example, the cannula 11 is 14 gauge. The cannula 11 can be formed from hypodermic needle stock. In certain embodiments, the surface of the cannula 11 is citric acid passivated.

In certain embodiments, the length of the cannula 11 from end of the beveled needle tip 110 (the proximal end) to the distal end of the cannula 11 is in the range of about 4.5 to about 7.7 inches, about 4.5 to about 6.5 inches, or about 4.9 to about 5.2 inches. In certain embodiments, the cannula 11 is about 5 inches long. Generally, the length of the cannula 11 inside the housing unit 12 is in the range of about 0.25 to about 0.35 inches, or about 0.30 inches. In certain embodiments, such as for obese patients, the length of the cannula 11 from end of the beveled needle tip 110 (the proximal end) to the distal end of the cannula 11 is in the range of about 5.7 to about 7.7 inches, or about 6.1 to about 6.4 inches.

In certain embodiments, the outer diameter of the cannula 11 is in the range of about 0.07 to about 0.09 inches, about 0.080 to about 0.086 inches, or about 0.082 to about 0.084 inches.

In certain embodiments, the inner diameter of the cannula 11 is in the range of about 0.06 to about 0.075 inches, about 0.065 to about 0.07 inches, or about 0.066 to about 0.069 inches.

In certain embodiments, the cannula 11 is slightly tapered, such that the diameter narrows from the distal end to the proximal end of the cannula. In certain embodiments, the outer diameter of the cannula 11 is in the range of about 0.07 to about 0.09 inches, about 0.080 to about 0.086 inches, or about 0.082 to about 0.084 inches at the distal end and narrows by about 0.002" at the proximal end prior to the beveled needle tip.

According to certain aspects of the present invention, the cannula 11 can be affixed to a housing unit 12 by any suitable means. In certain embodiments, the cannula 11 is affixed to a housing unit 12, for example, by mechanically via set screws, with adhesives, or a combination thereof. FIG. 5 shows a mechanical drawing of an exemplary housing unit 12.

During operation of the device 10, the housing unit 12 can be grasped by the physician for controlling the position and penetration of the device 10. A downward pressure sufficient to penetrate the device 10 into the body cavity is applied.

According to certain aspects of the present invention, the housing unit 12 contains a bore 121 of circular cross-section through the length of the device 10. In some embodiments, the diameter of the bore 121 is narrower at the distal end, as shown in FIG. 5. In certain embodiments, the housing unit 12 is about 0.5" in diameter at the proximal end and about 0.75 inches in diameter at the distal end. In some embodiments, the bore 121 passage through the housing is at least about 0.08 inches in diameter at its narrowest portions. Further, in some embodiments, the bore 121 passage through the housing unit 12 is at most about 0.32 inches in diameter at its widest portions, or large enough to accommodate the diameter of the spring cassette 15. Additional, narrow bore 122 passages may be included in the housing unit 12, which pass from one outer side to the center bore 121 at about 0.15 inches from the proximal end and about 3⁄16 inches from the distal end of the housing unit 12. In some embodiments, the housing unit 12 is substantially cylindrical, with an approximate diameter of about 0.5 inches, except for the most distal, about 3⁄8-inch, portion of the housing unit 12, which is about 0.75 inches in diameter and provides a handle for grasping the device 10.

According to certain aspects of the present invention, the housing unit 12 may be formed of any suitable material, such as, for example, metal or polymeric materials, such as, e.g., plastic. In some embodiments, the housing unit 12 is hollow and includes at least two slots 120 that extend axially along the housing unit 12. In certain embodiments, the slots align with the at least two pins 152 that extend from the blocking ring 151, which fits inside the housing unit 12 along with the spring cassette 15. In preferred embodiments, the slots 120 are of a length suitable to allow the stylet assembly 20 to be moved a short distance such as about 0.1 to about 0.2 inches, or about 0.15 inches, within the housing unit 12. In certain embodiments, the slots 120 are configured to engage with the pins 152 so as the prevent the stylet assembly 20 from moving too far in either the proximal or distal directions.

According to certain aspects of the present invention, the stylet 13 is positioned within the cannula 11. In some embodiments, the stylet 13 is a hollow tube with a proximal, rounded end (i.e., a dull tip) or a blunt tip 130 to protect any viscera from injury by the (sharp) cannula 11. In certain embodiments, the stylet 13 allows for gas to pass through the device 10—as in, through the hollow tube or lumen—and into the patient's body cavity (i.e., insufflation). The proximal end of the stylet 13 also includes suture-capturing feature, such as, for example, a hook or notch 131, for suture capturing (see FIG. 9). In some embodiments, a front compression spring 14 and spring cassette 15 is located at the distal end of the stylet 13 (see FIG. 8). The spring cassette 15 may include a rear compression spring 150 that is energized/de-energized to push out the proximal blunt stylet tip 130 into the extended configuration thereby blocking the beveled needle tip 110 of the cannula 11 against visceral damage after, e.g., entering the peritoneal cavity.

As referred to herein, the "stylet assembly" of the present invention may comprise a notch or hook 131 for suture capture; a front compression spring 14 encompassing the distal end of the stylet 13; a spring cassette 15; and a gas valve 16, e.g. a stopcock (see FIG. 6). In certain embodiments, the stylet assembly 20 may further comprise a gas connector 18. The stylet 13 is positioned inside the cannula 11 and housing unit 12.

In one embodiment, a spring cassette 15 (FIG. 7) comprises: (a) a rear compression spring 150; (b) a blocking ring 151 with at least two pins 152 protruding outward, which is distal to the rear compression spring 150; a distal cassette endcap 153 that is distal to the blocking ring 151; (c) a tubular support 154 flanked (i.e., adjacent to or abutted) by a proximal cassette endcap 155 and by a distal endcap 153.

In certain embodiments, the proximal cassette endcap 155 and distal endcap 153 are affixed to the tubular support 154 by adhesives. In certain embodiments, the rear compression spring 150 and blocking ring 151 are freely or loosely fitted on the tubular support 154 in between the two endcaps 153 and 155.

The movement of the blocking ring 151 with the pins 152 installed are restricted to slide forward and rearward along the two side slots 120 of the housing unit 12. In the rest position, the blocking ring 151 and pins 152 are located at the distal end of the side slots 120.

A section or portion of the outer wall of the stylet 13 is affixed to the inner lumen of the tubular support 154, for example, by adhesives. Thus, the spring cassette 15 (FIG. 7) is also affixed to the stylet 13 through the tubular support 154. The stylet 13 is therefore supported by the spring cassette 15, which can slide smoothly within the lumen of the housing unit 12. When the device 10 is inserted into the abdomen, the tissue resistance forces the stylet 13 backward and inward to expose the sharp, cutting tip of the cannula 11. Because the blocking ring 151 and pins 152 are located at the distal end of the side slots 120 and cannot move rearward, the inward movement of the stylet 13, along with the identical movement of the spring cassette 15, compresses and energizes the rear compression spring 150 located within the spring cassette 15. As the tissue resistance on the stylet tip 130 subsides upon entering into the peritoneal cavity, the rear compression spring 150 inside the spring cassette 15 deenergizes thereby pushing the stylet 13 outward and shielding the sharp cannula 11 tip to prevent viscera injury.

The gas valve 16 can be mounted directly on the distal endcap 153 or through an extension tube 17 and a gas connector 18 in case of the gas valve being located at right angle to the stylet 13.

In certain embodiments, the spring cassette 15 facilitates retraction of the hook or notch 131 of the stylet 130. That is, in some embodiments, the spring cassette 15 facilitates the stylet 13 moving into the retracted configuration.

At rest, or in the absence of contact, the blunt stylet tip 130 protrudes beyond the end of the sharp cannula 11 in the extended configuration, for example, by about 0.080 inches to about 0.100 inches. As the device 10 contacts the abdominal wall of the patient, the pressure on the blunt tip 130 of the stylet pushes it backwards into the cannula 11 and into the retracted configuration. Recessing of the spring-loaded stylet 13 exposes the sharp cannula tip 110 to pierce the skin and fascial layers of the abdominal wall. After the device 10 enters the peritoneal cavity, the tissue contact pressure suddenly drops and the compressed or energized spring 150, inside spring cassette 15, forces the stylet 13 forward into the extended configuration such that the stylet tip 130 protrudes beyond the cannula tip 110, thereby protecting any viscera inside the cavity from injury by the cannula tip 110. As such, the stylet 13 can be retracted by pressure or move forward via spring action.

According to certain aspects of the present invention, the blunt tip or rounded end of the hollow stylet 13 may be fabricated by a standard stainless-steel-tube end-forming technique. The closed end tube may be spun closed and welded shut by using standard tools and well-known tube forming procedures.

According to certain aspects of the present invention, the device 10 of the present invention comprises at least two springs, such as, for example, a front compression spring 14 for retraction of the notch or hook 131 and a rear compression spring 150 installed in a spring cassette 15.

In certain embodiments, distal to the rear compression spring 150 within the cassette 15 is a blocking-ring 151 (shown in FIG. 7) equipped with at least two anchoring pins 152 that protrude through the at least two slots 120 on the side walls of the housing unit 12 (FIGS. 4 and 5). The anchoring pins 152 can be, for example, threaded set screws (see FIG. 7) or non-threaded pins. Next to the blocking-ring 151 is an endcap 153 with an internal taper to connect with a gas valve 16, such as, for example, a male Luer slip of a stopcock. The gas valve 16 or stopcock also has a female Luer lock fitting for connection to an external gas (e.g., $CO_2$) supply line. In cases where the gas valve 16 is orthogonal to the stylet 13, an additional short extension tube 17 can be affixed to the distal endcap 153, which in turn attaches to a gas connector 18 to accomplish, e.g., a 90° turn for the gas valve 16 and gas supply line (FIG. 12).

When the device 10 is not in use, the blocking ring 151 is at a fixed position held by the at least two anchoring pins 152 (FIG. 7) to the rear ends of the side slots 120 on the housing unit 12. When the stylet 13 is pushed rearward, the blocking ring 151 does not move, but the spring cassette 15 moves backwards forcing the spring 150 to shorten and be compressed. The gas valve 16, which is attached to the spring cassette 15, also moves backwards.

Figure 7:
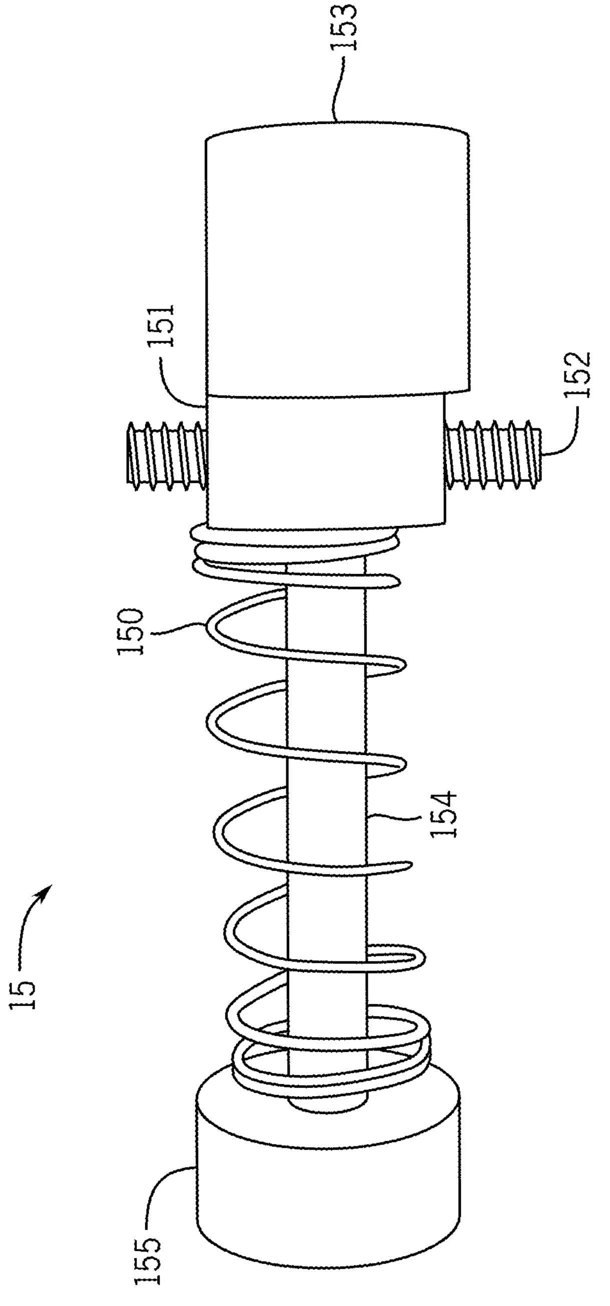
FIG. 7 is a photograph of an exemplary compression spring installed in a cassette according to certain embodiments of the present invention.

The stylet 13 is not affixed to the blocking ring 151, which can slide along the tubular support 154 (e.g., hollow tube) for the spring 150 (FIG. 7). The proximal end cap 155 of spring cassette 15 and the distal attachment for the gas valve 16 (e.g., stopcock) of the spring cassette 15 are attached to the tubular support 154. The stylet 13 is attached to the to the tubular support 154 via the inside wall (lumen) of the tubular support 154.

As the sharp cannula tip 110 enters the peritoneal cavity, the tissue pressure on the tip of the stylet 130 suddenly subsides, causing the energized rear compression spring 150 to expand and immediately pushing the stylet 13 back out again. As stated previously, the recovered stylet 13 position at the needle tip 110 shields the sharp cutting edge of the cannula 11 against visceral damage and injury upon entering the abdomen. Following entry into the peritoneal cavity, the gas valve 16 can be switched on to introduce gas for insufflation of the body cavity and for establishment of pneumoperitoneum for laparoscopic surgery.

According to certain aspects of the present invention, following suture placement, the hook or notch 131 retraction is automatically accomplished via spring action as soon as the forward pushing force is released. In some embodiments, the mechanical properties of the front compression spring 14 are chosen such that the gap closes rapidly to ensure secure capturing of the suture placed inside the gap.

According to certain aspects of the present invention, the device 10 comprises a gas valve 16 (also referred to herein as a "stopcock") that can be used to start or stop the flow of gas (e.g. $CO_2$) into the patient. When the device 10 is inserted into the peritoneal cavity, the flow of gas can be switched on by means of a gas valve 16 to inflate the cavity and create pneumoperitoneum for laparoscopic surgery.

At the conclusion of surgery, at least one surgical device, for example a trocar, is retracted from the abdomen, leaving a puncture wound. In certain embodiments, the size of the wound may be about the diameter of the cannula 11 or shaft of the surgical device. In certain embodiments, the wound (e.g. a proximal wound, referred to herein) is larger than about 5 mm and needs to be closed. This wound site may be closed through approximation of tissue by percutaneous suturing. Instead of conducting time-consuming surgical suturing or utilizing a separate device for wound site closure, the device 10 according to certain aspects of the invention can be used to facilitate wound closure through a suture-capturing hook or notch. Because a suture can be captured, held, externalized, and internalized, two ends of the suture can be positioned and externalized across the wound. The suture ends are then pulled tight and knotted to close the wound. In addition to externalization, a suture can also be internalized by first capturing it outside the patient's body, puncturing through the exposed wound fascia from one side, looping around the wound internally, and externalizing from the opposite side of the wound before knotting. In this way, the physician may achieve easy site closure using the present invention.

Figure 17:
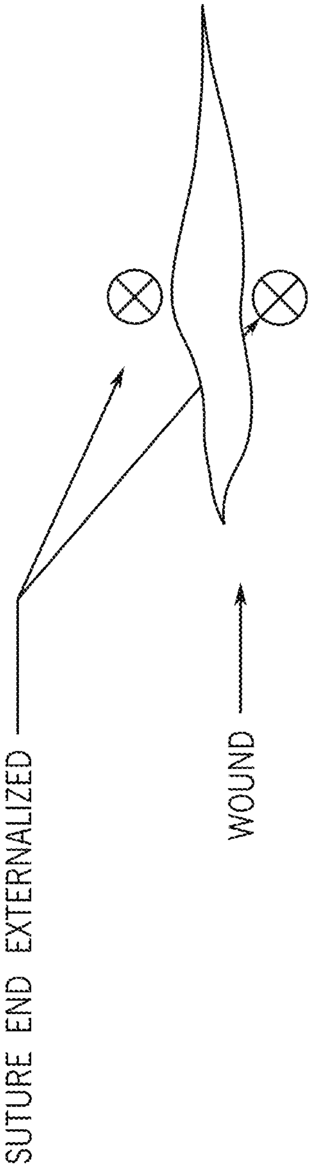
FIG. 17 and FIGS. 18A and 18B (collectively, FIG. 18) shows illustrations of suture positions for wound closure according to certain embodiments of the present invention.

In one embodiment, wound closure proceeds by the following process:

(i) externalize two ends of a suture from opposite sides of a wound (FIG. 17);
(ii) insert the exemplary device 10 proximal to a wound,
(iii) capture or hold end of a first suture end from inside body cavity,
(iv) externalize the first suture end for knotting outside the wound; and
(v) repeat steps (iii) and (iv) for second suture end.

In certain embodiments, the exemplary device 10 can enter through the fascia layer beneath the skin of the wound.

In certain embodiments, the suture thread (for example, suture thread with no metal cutting needle attached) is introduced inside body, through a trocar, prior to wound closure procedure.

Figure 18A:
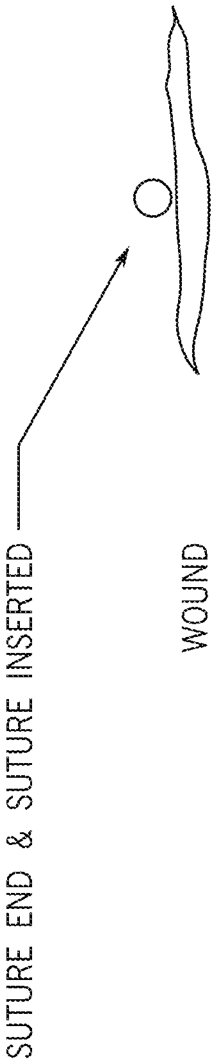
Figure 18B:
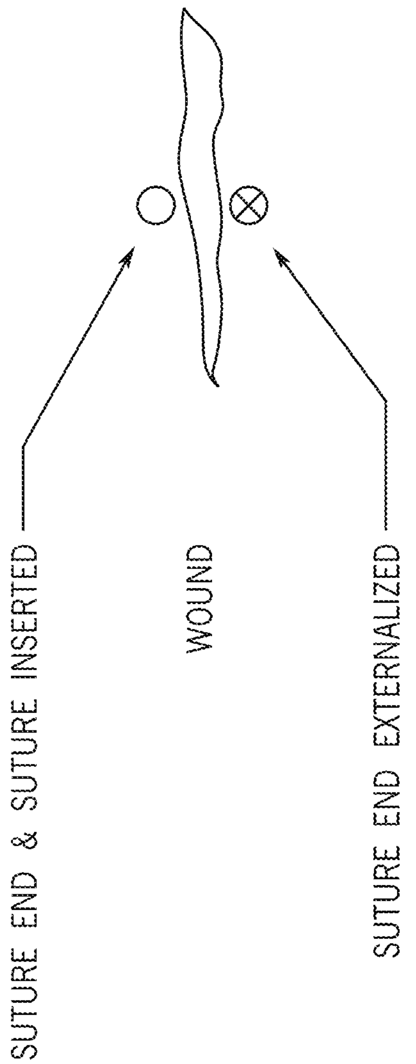
Figure 19B:
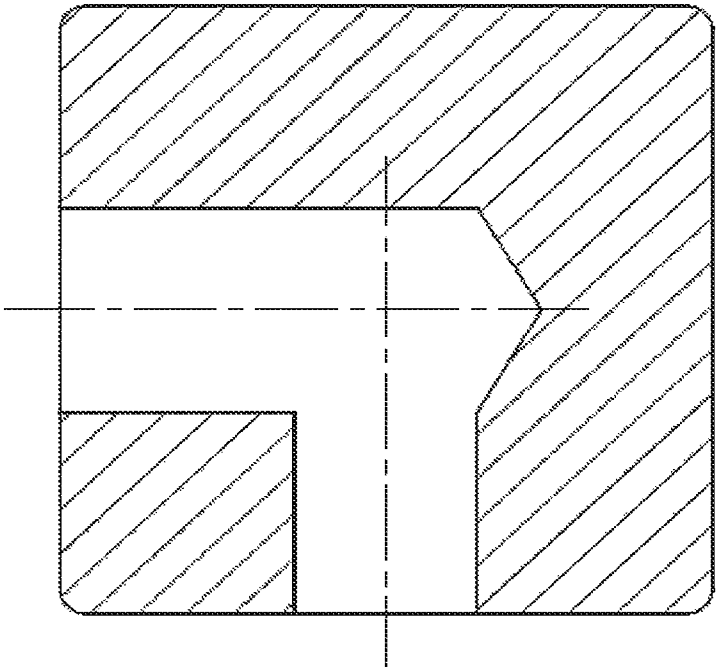
FIGS. 19A and 19B (collectively, FIG. 19) are drawings showing an exemplary gas connector according to certain embodiments of the present invention.
Figure 19A:
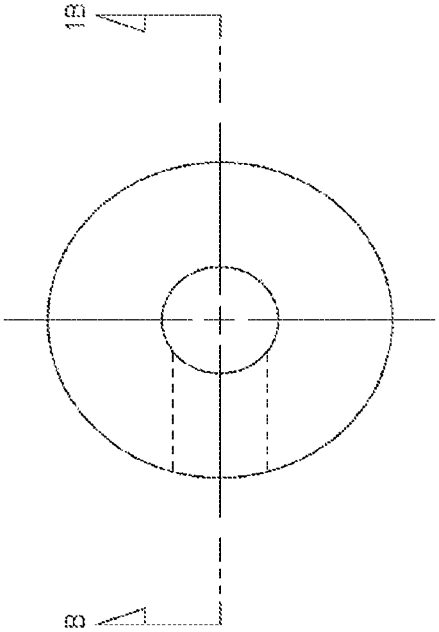
Figure 20B:
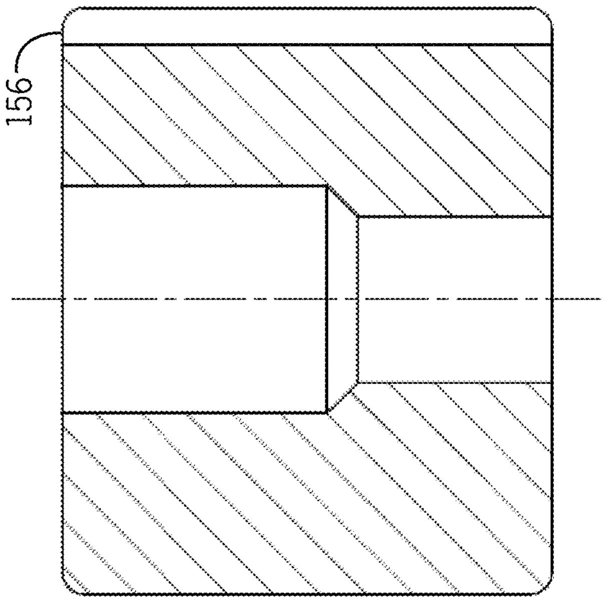
FIGS. 20A and 20B (collectively, FIG. 20) are drawings showing an exemplary spring cassette endcap according to certain embodiments of the present invention.
Figure 20A:
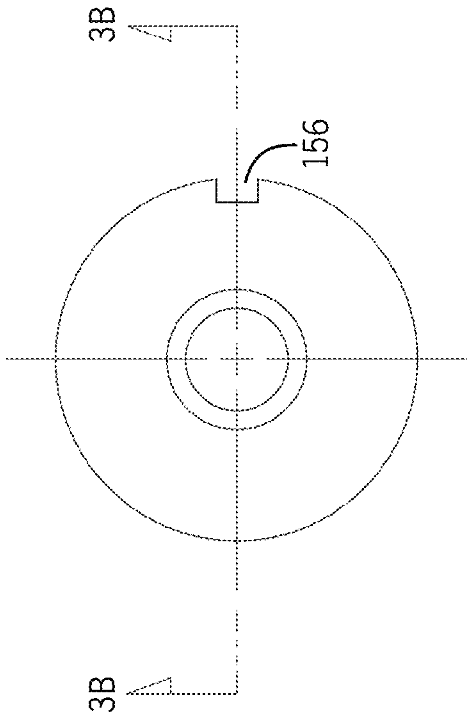
Figure 21B:
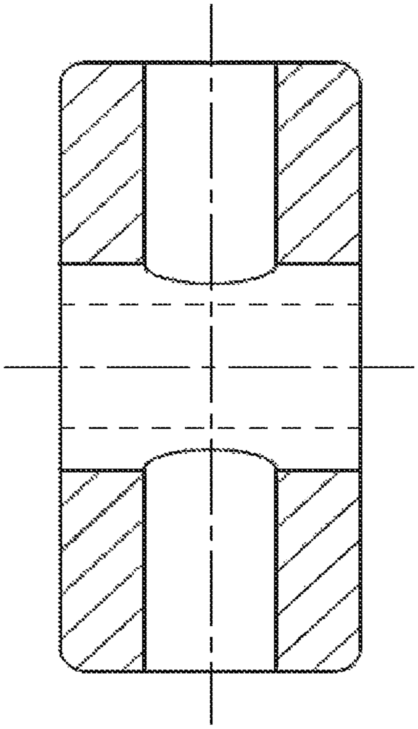
FIGS. 21A and 21B (collectively, FIG. 21) are drawings showing an exemplary blocking ring according to certain embodiments of the present invention.
Figure 21A:
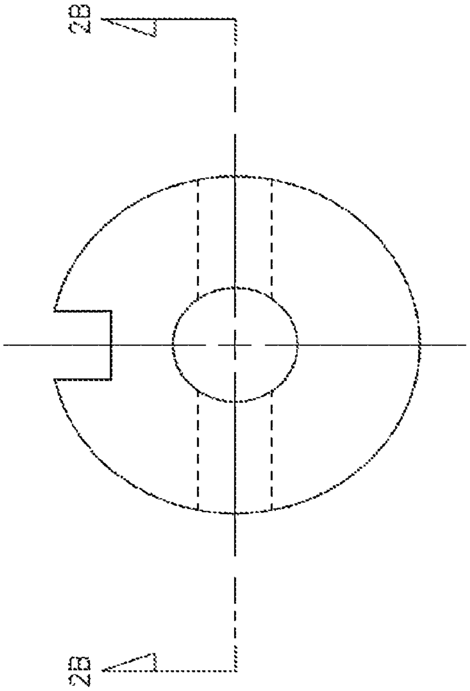

In one embodiment, wound closure proceeds by the following process:

(i) internalize one suture end plus the entire suture thread from one side of a wound (FIG. 18);

(ii) externalize the suture end from opposite side of wound with exemplary device 10 (e.g., from outside of body, capture and hold one end of suture with exemplary device 10).

In certain embodiments, wound closure proceeds by the following process:

(i) inserting a suture into a body next to one side of wound with the exemplary device 10 or a surgical device to internalize a suture while leaving one end of the suture out of the body, (ii) inserting the exemplary device 10 (empty; without a suture) into the body from the opposite side of the wound to capture the internalized suture;

(iii) externalizing the other end of the suture for knotting.

In certain embodiments, the stylet 13 can be manually pushed forward (e.g. beyond the resting or neutral position) to capture a suture for wound closure. The stylet 13 may be equipped with a hook 131 (for example, a hook that resembles a crochet needle hook) for suture capture. In certain embodiments, the hook 131 is shaped as a notch in the stylet 13.

To capture a suture, the stylet tip 130 can be pushed forward, for example, via the gas valve 16, or a handle or button 19 that may be attached to the gas valve 16 to catch a suture on the notch or hook 131. In certain embodiments, where the gas valve is orthogonal to the stylet 13 (FIG. 12), the gas connector 18 may also serve as a handle for pushing the stylet tip 130 forward. The notch or hook 131 securely holds the suture after automatic retraction by spring action when the pushing force is released.

Figure 8:
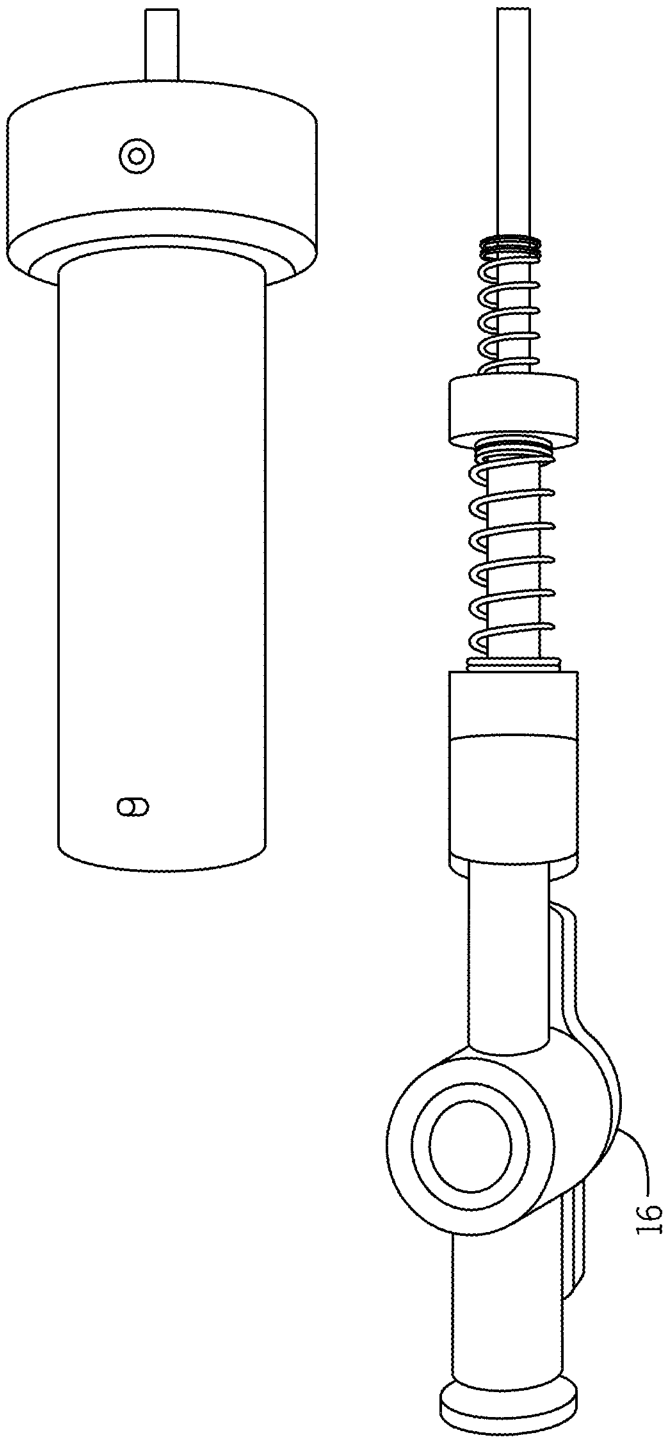
FIG. 8 is a photograph showing an anti-rotation pin installed on an exemplary housing unit and a female slot located between stopcock and spring cassette according to certain embodiments of the present invention.
Figure 9A:
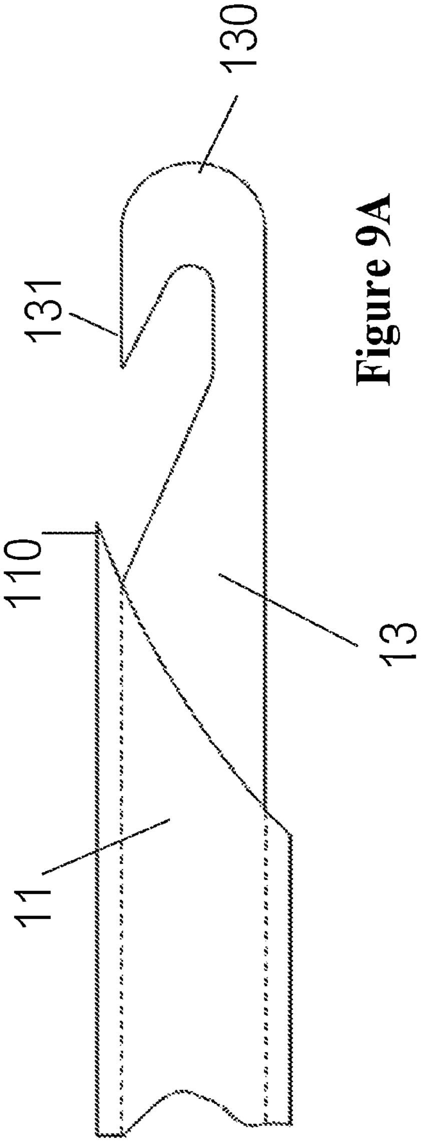
FIGS. 9A and 9B (collectively, FIG. 9) are drawings showing the exemplary stylet and hook, advanced forward to catch a suture (FIG. 9A) or in the closed or retracted position to capture a suture (FIG. 9B) according to certain embodiments of the present invention.
Figure 9B:
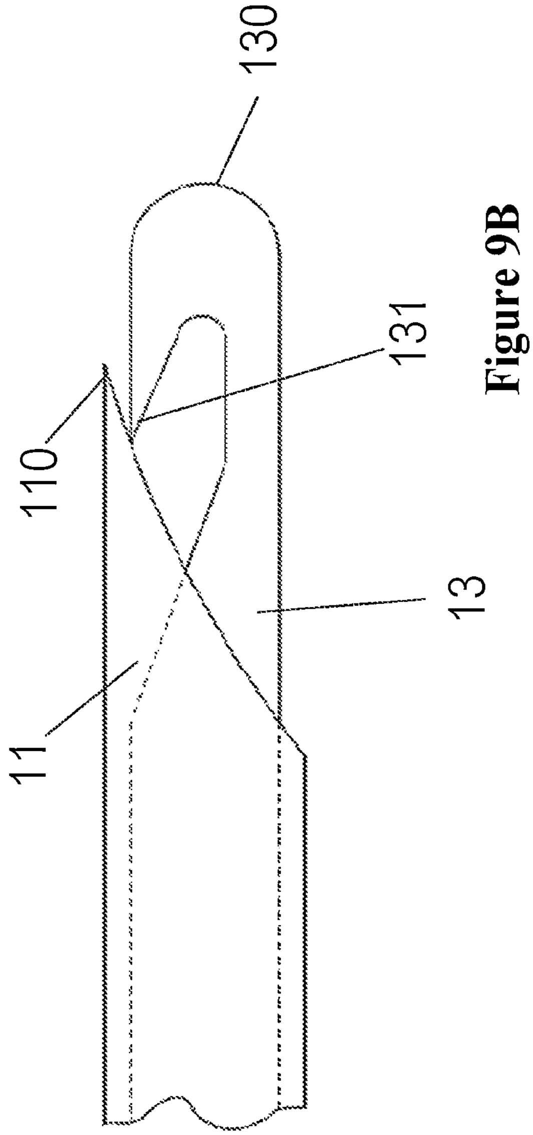
Figure 10:
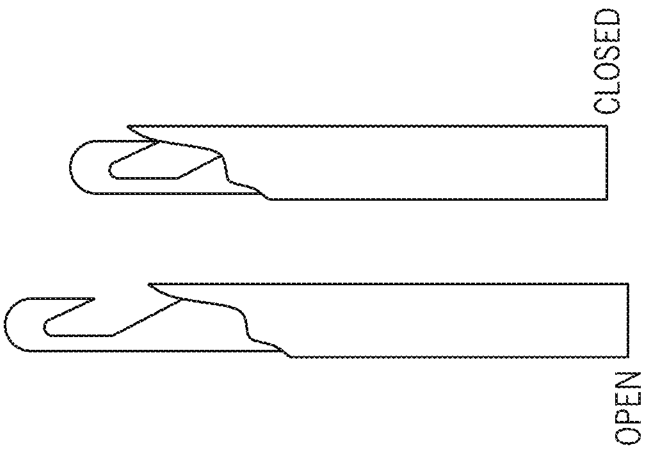
FIG. 10 is a black and white photograph of an exemplary hook in extended (open) and retracted (closed) positions according to certain embodiments of the present invention.
Figure 11:
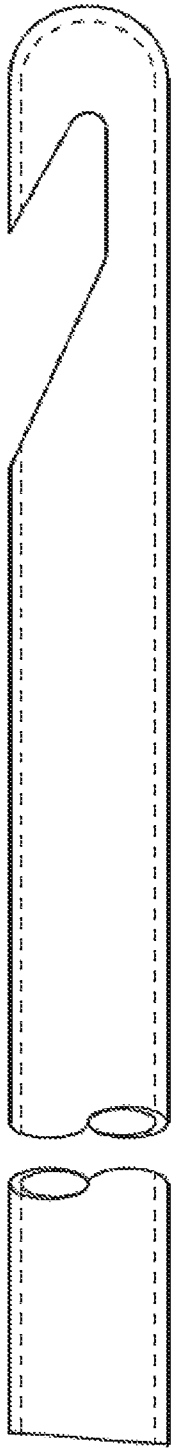
FIG. 11 is a drawing of an exemplary hook according to certain embodiments of the present invention.

According to certain aspects of the present invention, the forward push advances the blocking ring 151 together with the tip 130 of the stylet 13, thereby creating a gap to allow catching of a suture thread (see FIGS. 9 and 10). The forward displacement of the stylet 13 is limited by the width of the side slots 120 where the anchoring pins 152 are protruding (see FIGS. 3, 4 and 5). In addition to the rear compression spring 150 installed in the spring cassette 15, there is a front compression spring 14 (see FIG. 6) located next to the proximal spring cassette end cap 155 of the cassette. This front compression spring 14 is used to retract the stylet 13 and capture the suture placed inside the gap of the hook 131, when the gas valve 16 is no longer being pushed. FIGS. 9 and 10 show the hook 131 in the open position when the device 10 is pushed forward (i.e., ready to receive/capture a suture) and also the hook 131 in the closed position (retracted, rest or neutral position) capable of securely holding any suture placed inside the gap. The captured suture is enclosed within the small cavity bounded by the hook 131 and the cutting edge of the cannula tip 110. As the opening, where the suture is entrapped, is bounded by the hook 131 and the bevel tip of the cannula 110, the angular position (i.e., rotational position) of the stylet 13 relative to the cannula 11 is maintained by an anti-rotation pin 123 of the housing unit 12 together with an anti-rotation slot 156 formed on the distal endcap 153 as shown in FIG. 8. The anti-rotation pin 123 is visible on the distal end of housing unit 12 and the anti-rotation slot 156 is visible on the distal endcap 153.

In certain embodiments, the device 10 is used to capture, hold, pass, externalize, and internalize a suture. In certain embodiments, the device 10 is used to close a wound left by a retracted laparoscopic device. Closing a wound according to the embodiments can be accomplished by a procedure via approximation of tissues and percutaneous suturing for closure of a wound or puncture site without using the standard suture needle (using only the suture thread). Two ends of a suture can be positioned mechanically approximating the opposite edges of a wound ready for closure. The externalized ends of a suture are used to bind both fascia, and subcutaneous tissue and, optionally, skin. In certain embodiments, the abdominal wall is elevated by pulling the two ends of suture from opposite sides of wound upwards, tightened, and knotted to complete the closure. The suture can be introduced inside the abdominal cavity with standard illumination and visualization by an inserted camera. Alternatively, the suture can be captured outside, held by the needle device 10, and subsequently inserted into the abdominal cavity near the wound site.

The hook 131 can be formed by laser or mechanical cutting.

In one embodiment, the device 10 comprises:

(i) a cannula 11 comprising a beveled needle tip 110 at a proximal end and attached to a housing unit 12 at a distal end;

(ii) a blunt-tipped stylet 13 comprising a hook or notch 131 at the proximal end of the stylet and supported within the cannula;

(iii) a gas valve 16, positioned distal to the housing unit 12, configured to introduce of gas at the proximal end of the cannula;

(iv) a front compression spring 14 encompassing the distal end of the stylet 13;

(v) a spring cassette 15 comprising:

a rear compression spring 150;

a blocking ring 151 with two pins 152 protruding outward, which is distal to the rear compression spring 150;

a distal cassette endcap 155, which is distal to the blocking ring 151;

a tubular support 154 flanked by a proximal cassette endcap 155 and by a distal gas valve 16, the tubular support 154 situated in the interior of the rear compression spring 15, blocking ring 151 and distal endcap 155;

wherein the stylet 13, front compression spring 14 and spring cassette 15 are inserted through the distal end of the housing unit 12 and into the cannula 11 so that the proximal end of the stylet 13 protrudes beyond the cannula tip 110;

wherein the housing unit 12 comprises two side slots 120 into which the two pins 123 protruding outward from the blocking ring 151 fit, wherein the stylet 13 retracts into the cannula 11 when the device 10 is pressed into a body wall of a patient;

wherein the stylet 13 springs forward beyond the cannula tip 110 after the cannula tip 110 has penetrated through the body wall and into a body cavity;

wherein insufflation gas is introduced into the body cavity through the gas valve 16 and stylet 13; and wherein the hook or notch 131 can be retracted to capture a suture.

Methods of Use

Figure 2:
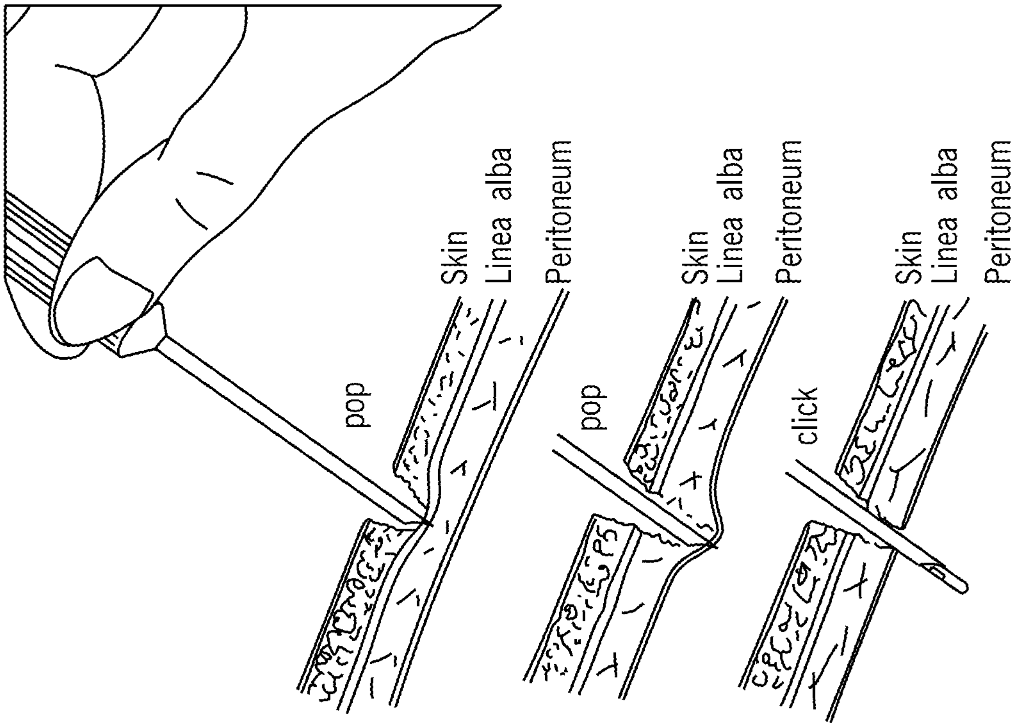
FIG. 2 is an illustration of the audio-vibrational feedback of the penetration of the Veress needle into the peritoneal cavity, in accordance with the embodiments of the invention.

Generally, the exemplary device 10 can be used, as a Veress needle, for penetration of a body cavity wall, e.g., the peritoneal wall. The contact pressure exerted by body cavity wall on the stylet of the device 10 pushes the stylet 13 into the inner lumen of the cannula 11, exposing the beveled needle tip 110 of the cannula 11 to penetrate the body cavity wall. After the cannula 11 pierces through the skin/fascia and enters the body (e.g., peritoneal) cavity, the stylet 13 springs forward to block the cannula tip 110, thereby protecting internal viscera from injury by the sharp cannula 11. The penetration of the exemplary device 10 of the present invention into the peritoneal cavity carries unique audio-vibrational feedback to the surgeon (FIG. 2).

After the exemplary device 10 enters the body cavity, gas (e.g., $CO_2$) can then be passed through the hollow lumen of the stylet to insufflate the body cavity. Insufflation of the body cavity is carried out to create space for the laparoscopic surgery. In the example of a peritoneal cavity, insufflation of the peritoneal cavity with $CO_2$ gas creates a pneumoperitoneum for ease of laparoscopic surgery.

At conclusion of laparoscopic surgery, the exemplary device 10 of the present invention is retracted, ready for use to close, by suture, open wounds left by trocars, probes and other large diameter devices retracted after surgery.

In certain embodiments, the exemplary device 10 of the present invention can be employed to introduce and place a suture without requiring a separate device. The hook or notch of the exemplary device 10 can be used to introduce a suture, which is secured in the hook or notch 131 in the retracted position, into a proximal wound. The suture can be applied to the proximal wound by maneuvering the exemplary device 10 and externalized from inside the body cavity across the wound (e.g., incision) location. The two ends of a suture are then pulled up, tightened, and knotted from outside to complete the closure of a wound left by an extracted, large bore device, such as a trocar. According to certain embodiments, the exemplary device 10 may be used to close a wound by externalizing two ends of a suture from opposite sides of the wound. This is done by puncturing respectively the exemplary device 10 through sides of wound, grasping and capturing the suture, pulling the end of suture out from inside the abdomen, and tying the externalized suture ends together into a tight knot to close the wound by tissue approximation. For this operation, a suture with two free ends must be pre-introduced inside the abdomen via a trocar port. Alternatively, the suture can be internalized from one side of wound and the end of suture is then externalized from the opposite side before knotting. In certain embodiments, the end of a suture is first captured by the exemplary device 10 from outside the body before puncturing and carrying the entire suture into the abdomen from one side of the wound to complete the suture internalization process.

In certain embodiments, a separate device like a trocar is then employed to introduce a suture inside the body cavity (e.g. peritoneal cavity). The hook or notch 131 of the exemplary device 10 can then be used to capture the suture by pushing forward the stylet assembly 20. By pushing the stylet assembly 20 forward, the hook or notch 131 opens a gap to receive and capture the suture. The front compression spring 14 is used to retract the stylet hook 131 and capture the suture placed within the gap space (see FIGS. 9 and 10). The suture is externalized by the exemplary device 10 from inside the body cavity across the wound (e.g., incision) location. The two ends of a suture are then pulled up, tightened, and knotted from outside to complete the closure of a proximal wound by the exemplary device 10.

Certain embodiments of the invention also provide a method for laparoscopic access and wound closure in a patient in need thereof. In one embodiment, the method comprises: (a) penetrating a body cavity through a body wall with a device 10 to form an opening, the device 10 comprising:

(i) a cannula 11 comprising a and a beveled needle tip 110 at a proximal end and attached to a housing unit 12 at a distal end;

(ii) a blunt-tipped stylet comprising a hook or notch 131 at the proximal end and supported within the cannula 11;

(iii) a gas valve 16, positioned distal to the housing unit 12, configured to introduce of gas at the proximal end of the cannula 11;

(iv) a front compression spring 14 encompassing the distal end of the stylet 13;

(v) a spring cassette 15 comprising a rear compression spring 150; blocking ring 151 with two pins 152 protruding outward, which is distal to the rear compression spring 150; distal cassette endcap 153, which is distal to the blocking ring 151; a tubular support 154 flanked by a proximal cassette endcap 155 and by the gas valve 16 on the distal end, situated in the interior of the rear compression spring 150, blocking ring 151 and distal endcap 153;

wherein the stylet 13, front compression spring 14 and spring cassette 15 are inserted through the distal end of the housing unit 12 and into the cannula 11 so that the proximal end of the stylet protrudes beyond the cannula tip 110;

wherein the housing unit 12 comprises two side slots 120 into which the two pins 152 protruding outward from the blocking ring 151 fit, wherein the stylet 13 retracts into the cannula 11 when the device 10 is pressed into a body wall of a patient;

wherein the stylet 13 springs forward beyond the cannula tip 110 after the cannula tip 110 has penetrated through the body wall and into a body cavity;

wherein insufflation gas is introduced into the body cavity through the gas valve 16 and stylet 13; and wherein the hook or notch 131 can be retracted to capture a suture;

(b) insufflating the cavity with gas through the opening;

(c) maneuvering the stylet 13 of the device 10 to capture a suture in the body cavity; and (d) positioning the suture across a proximal wound and externalizing the suture to close off the proximal wound.

In certain embodiments, the suture is introduced into the body cavity through a separate port device such as a trocar. In certain embodiments, the step of maneuvering the stylet of the device 10 to capture a suture for wound closure occurs after introduction of a suture (e.g. material for the suture) into the body cavity through a separate port.

In certain embodiments, the suture is introduced into the body cavity by a process of suture internalization as previously described using the exemplary device 10. A suture is held and/or captured by the exemplary device 10 outside the body and subsequently punctured through the body wall (e.g., abdominal wall) into the body cavity for use in wound closure.

In certain embodiments, the step of maneuvering the stylet of the device 10 to comprising pushing forward the stylet.

It will be apparent to those skilled in the art that many modifications and substitutions can be made to the embodiments described above without departing from the spirit and scope of the present invention.

What is claimed is:

1. A device comprising:

(i) a cannula comprising a beveled needle tip at a proximal end and attached to a housing unit at a distal end;

(ii) a blunt-tipped stylet comprising a hook or notch at the proximal end of the stylet and supported within the cannula;

(iii) a distal gas valve, positioned distal to the housing unit, configured to introduce of gas at the proximal end of the cannula;

(iv) a front compression spring encompassing the distal end of the stylet;

(v) a spring cassette comprising:

a rear compression spring;

a blocking ring with two pins protruding outward, which is distal to the rear compression spring, wherein the blocking ring is in contact with both of the front compression spring and the rear compression spring;

a distal cassette endcap, which is distal to the blocking ring;

a tubular support flanked by a proximal cassette endcap and by the distal gas valve, the tubular support situated in the interior of the rear compression spring, blocking ring and distal endcap;

wherein the stylet, front compression spring and spring cassette are inserted through the distal end of the housing unit and into the cannula so that the proximal end of the stylet protrudes beyond the cannula tip;

wherein the housing unit comprises two side slots into which the two pins protruding outward from the blocking ring fit to slide distally and proximally therein, wherein the stylet retracts into the cannula when the device is pressed into a body wall of a patient;

wherein the stylet springs forward beyond the cannula after the cannula tip has penetrated through the body wall and into a body cavity;

wherein insufflation gas is introduced into the body cavity through the gas valve and the stylet; and wherein the hook or notch is configured to be retracted to capture a suture.

2. The device of claim 1, wherein the blunt-tipped stylet comprises a hook.

3. The device of claim 1, wherein the blunt-tipped stylet comprises a notch.

4. The device of claim 1, wherein the gas valve comprises a stopcock.

5. The device of claim 1, wherein the gas valve is distally mounted on the housing unit and in an axial position.

6. The device of claim 1, wherein the gas valve is mounted on the housing unit and in an orthogonal position.

7. The device of claim 1, wherein the two pins protruding outward from the blocking ring comprises screws.

8. The device of claim 1, wherein the two pins protruding outward from the blocking ring comprises solid pins.

9. The device of claim 1, wherein the body cavity is a peritoneal cavity.

10. The device of claim 1, wherein the stylet comprises an elongated sleeve having a hollow lumen extending along its length, wherein the hollow lumen is configured to allow passage of insufflation gas into the body cavity.

11. The device of claim 1, wherein the blunt tip of the stylet is flat or rounded.

12. The device of claim 1, wherein the gas valve comprises a luer lock fitting for connection to an external gas supply line.

13. A method for laparoscopic access and wound closure in a patient in need thereof, the method comprising:

penetrating a body cavity through a body wall with a device to form an opening, the device comprising:

(i) a cannula comprising a beveled needle tip at a proximal end and attached to a housing unit at a distal end;

(ii) a blunt-tipped stylet comprising a hook or notch at the proximal end and supported within the cannula;

(iii) a distal gas valve, positioned distal to the housing unit, configured to introduce gas at the proximal end of the cannula;

(iv) a front compression spring encompassing the distal end of the stylet;

(v) a spring cassette comprising a rear compression spring; a blocking ring with two pins protruding outward, which is distal to the rear compression spring; a distal cassette endcap, which is distal to the blocking ring; a tubular support flanked by a proximal cassette endcap and by the distal gas valve, situated in the interior of the rear compression spring, the blocking ring and the distal endcap;

(vi) wherein the stylet, front compression spring and spring cassette are inserted through the distal end of the housing unit and into the cannula so that the proximal end of the stylet protrudes beyond the cannula tip and the blocking ring contacts the both of the front compression spring and the rear compression spring;

(vii) wherein the housing unit comprises two side slots into which the two pins protruding outward from the blocking ring fit to slide distally and proximally therein, (viii) wherein the stylet retracts into the cannula when the device is pressed into a body wall of a patient;

(ix) wherein the stylet springs forward beyond the cannula tip after the cannula tip has penetrated through the body wall and into a body cavity;

(x) wherein insufflation gas is introduced into the body cavity through the gas valve and stylet; and (xi) wherein the hook or notch is configured to be retracted into the cannula to capture a suture;

insufflating the cavity with gas through the opening;

maneuvering the stylet of the device to capture a suture in the body cavity; and positioning the suture across a proximal wound and externalizing the suture to close off the proximal wound.

14. The method of claim 13, wherein the suture is introduced into the body cavity by a separate suture device.

15. The method of claim 13, wherein the step of maneuvering the stylet of the device to capture a suture for wound closure occurs after a separate suture device has introduced a suture into the body cavity.

16. The method of claim 13, the step of maneuvering the stylet of the device to comprising pushing forward the stylet.

17. The method of claim 13, further comprising receiving audio-vibrational feedback upon penetration of the body cavity by the cannula tip.

18. The method of claim 13, wherein the insufflation gas comprises carbon dioxide.

19. The method of claim 13, wherein insufflating the cavity creates a pneumoperitoneum for laparoscopic surgery.

20. The method of claim 13, wherein capturing the suture comprises retracting the hook or notch via the front compression spring.

* * * * *